United States Patent
Aoyama et al.

(10) Patent No.: US 6,680,326 B2
(45) Date of Patent: Jan. 20, 2004

(54) POLYCYCLIC COMPOUNDS

(75) Inventors: Tsunehisa Aoyama, Fujisawa (JP);
Kenichi Kawasaki, Fujisawa (JP);
Miyako Masubuchi, Yokohama (JP);
Tatsuo Ohtsuka, Kamakura (JP);
Kiyoaki Sakata, Sagamihara (JP)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/254,951

(22) Filed: Sep. 25, 2002

(65) Prior Publication Data

US 2003/0073691 A1 Apr. 17, 2003

(30) Foreign Application Priority Data

Oct. 5, 2001 (EP) .............................. 01123908

(51) Int. Cl.[7] .................... A61K 31/473; A61K 31/435; C07D 471/02
(52) U.S. Cl. ........................ 514/285; 546/70; 546/65; 546/58; 544/233; 544/246; 544/343; 514/280; 514/257; 514/250; 514/248
(58) Field of Search ................. 514/285, 287, 514/280, 257, 250, 248; 546/70, 58, 65; 544/233, 246, 343

(56) References Cited

FOREIGN PATENT DOCUMENTS

| EP | 713 870 | 5/1996 |
|---|---|---|
| EP | 1 101 765 | 5/2001 |
| WO | WO 98 45272 | 10/1998 |

OTHER PUBLICATIONS

Allan et al., Aust. J. Chem., 36, pp. 1221–1226 (1983).

Binder, D., Monatshefte für Chemie, 105, pp. 179–186 (1974).

*Primary Examiner*—C. S. Aulakh
(74) *Attorney, Agent, or Firm*—George W. Johnston; Patricia S. Rocha-Tramaloni; Bernard Lau

(57) ABSTRACT

Novel polycyclic compounds of the formula [I],

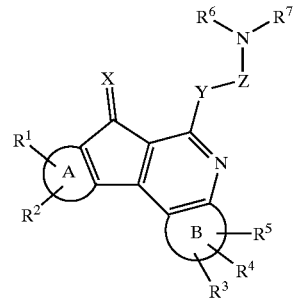

wherein $R^1$, $R^2$, $R^3$, $R^4$, $R^5$, $R^6$, $R^7$, ring A, ring B, X, Y and Z are as defined herein and the pharmaceutically acceptable salts thereof. These compounds have antitumor activity and useful for the treatment of cancer.

35 Claims, No Drawings

POLYCYCLIC COMPOUNDS

FIELD OF THE INVENTION

The present invention relates to novel polycyclic compounds having anti-tumor activity, pharmaceutical composition containing these compounds, the use of these compounds in the medical therapy as well as a process for the preparation of these compounds.

BACKGROUND OF THE INVENTION

Indeno[2,1-c]quinolin-7-one derivatives having a substituted aminoalkylamino radical as a side chain are known to have anti-tumor activity. For example, 6-(2-dimethylamino-ethylamino)-3-hydroxy-7H-indeno[2,1-c]quinolin-7-one and its derivatives have been disclosed to have anti-tumor activity. See, EP 0713870 (1996). However, anti-tumor activity in this reference may not be sufficient for the treatment of tumor and thus, more potent anti-tumor compounds are desirable.

It is therefore advantageous in the art to provide more potent anti-tumor compounds for treatment of tumor.

SUMMARY OF THE INVENTION

The present invention is directed to novel polycyclic compounds of the formula [I],

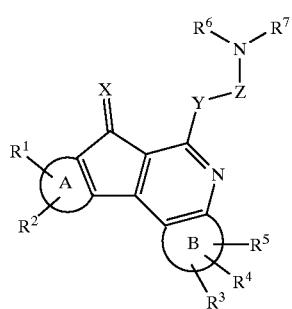

wherein;

ring A is a nitrogen-containing 5 or 6 membered heteroaromatic ring which may be substituted by $R^1$ and $R^2$;

$R^1$ and $R^2$ are independently hydrogen, halogen, (C1–C5) alkyl, hydroxy, mercapto, (C1–C5) alkoxy, (C4–C7) cycloalkyloxy, (C3–C7)cycloalkyl(C1–C5)alkyloxy, (C1–C5) alkylthio, (C1–C5) alkylsulfinyl, (C1–C5) alkylsulfonyl, amino, mono-(C1–C5)-alkylamino, di-(C1–C5)-alkylamino or —Y'—Z'—N($R^{6'}$)($R^{7'}$);

wherein

Y' is O, S or N($R^{9'}$), wherein $R^{9'}$ is hydrogen or (C1C5) alkyl; or when Y' is N($R^{9'}$), N($R^{9'}$) forms an aliphatic ring together with N($R^{6'}$) and Z';

Z' is (C2–C5) alkylene; or Z' forms an aliphatic ring together with N($R^{6'}$) and (N$R^{9'}$); or Z' forms an aliphatic ring together with N($R^{6'}$);

$R^{6'}$ and $R^{7'}$ are independently hydrogen, (C1–C5) alkyl, (C3–C5) alkenyl, (C4–C7) cycloalkyl, (C3–C7) cycloalkyl(C1–C5)alkyloxy or aryl(C1–C5)alkyl optionally substituted with one to three substituents selected from the group consisting of hydroxy, (C1–C5) alkoxy, amino, mono-(C1–C5)-alkylamino and di-(C1–C5)-alkylamino radical(s); or $R^{6'}$ and $R^{7'}$ form an aliphatic ring optionally containing one to three heteroatom(s) selected from oxygen, nitrogen and sulfur together with the adjacent nitrogen; or $R^{6'}$ forms an aliphatic ring together with the adjacent nitrogen and Z'; or $R^{6'}$ forms an aliphatic ring together with the adjacent nitrogen, N($R^{9'}$) and Z';

ring B is a benzene ring, naphthalene ring or benzene ring substituted with (C1–C5) alkylenedioxy group which is optionally substituted by $R^3$, $R^4$ and $R^5$;

$R^3$, $R^4$ and $R^5$ are independently hydrogen, halogen, hydroxy, mercapto, (C1–C5) alkyl, (C1–C5) halogenoalkyl, (C1–C5) alkoxy, (C1–C5) halogeno-alkoxy, (C3–C5) alkenyloxy, (C4–C7) cycloalkyloxy, (C3–C7) cycloalkyl(C1–C5)alkyloxy, aryl(C1–C5)alkyloxy, (C1–C5) alkylthio, (C1–C5) alkylsulfinyl, (C1–C5) alkylsulfonyl, amino, mono-(C1–C5)-alkylamino or di-(C1–C5)-alkylamino;

X is O or N—O—$R^8$ wherein $R^8$ is a hydrogen, (C1–C5) alkyl, (C3–C5) alkenyl, (C4–C7)cycloalkyl, (C3–C7) cycloalkyl(C1–C5)alkyloxy, aryl, or aryl(C1–C5)alkyl;

Y is O, S or N($R^9$) wherein $R^9$ is hydrogen or (C1–C5) alkyl; or when Y is N($R^9$), N($R^9$) forms an aliphatic ring together with N($R^6$) and Z;

Z is (C2–C5) alkylene optionally substituted with (C1–C5) alkyl radical(s); or Z forms an aliphatic ring together with N($R^6$) and N($R^9$); or Z forms an aliphatic ring together with N($R^6$);

and $R^6$ and $R^7$ are independently hydrogen, (C1–C5) alkyl, (C3–C5) alkenyl, (C4–C7) cycloalkyl, (C3–C7) cycloalkyl(C1–C5)alkyloxy or aryl(C1–C5)alkyl optionally substituted with hydroxy, (C1–C5) alkoxy, amino, mono-(C1–C5)-alkylamino or di-(C1–C5)-alkylamino radical(s); or $R^6$ and $R^7$ form an aliphatic ring optionally containing one to three heteroatom(s) selected from oxygen, nitrogen and sulfur together with the adjacent nitrogen; or $R^6$ forms an aliphatic ring together with the adjacent nitrogen and Z; or $R^6$ forms an aliphatic ring together with the adjacent nitrogen, N($R^9$) and Z, as well as pharmaceutically acceptable salts thereof.

This invention is also directed to a pharmaceutical composition containing the above-described compounds, and a method for treating a cell proliferative disorder, especially in treatment of tumor, comprising administering to a patient in need thereof a therapeutically effective amount of the above-described compounds.

This invention is also directed to providing a process for the preparation of those compounds.

DETAILED DESCRIPTION OF THE INVENTION

Unless otherwise indicated, the following definitions are set forth to illustrate and define the meaning and scope of the various terms used to describe the present invention herein.

In this specification, the term "nitrogen-containing 5 or 6 membered heteroaromatic ring" is used to mean a radical of a 5 to 6 membered aromatic ring which contains at least one nitrogen atom and may further contain one or more heteroatom(s) selected from N, S and O. Preferably, "nitrogen-containing 5 or 6 membered heteroaromatic ring" means pyridine, pyrazine, pyridazine, pyrimidine, oxazole, thiazole, isoxazole, isothiazole, imidazole, pyrrole, triazole and the like, and more preferably, pyridine.

The term "alkyl" as used herein, alone or in combination, means a straight-chain or branched-chain hydrocarbon group containing a maximum of 12, preferably a maximum of 5, carbon atoms, e.g., methyl, ethyl, n-propyl, 2-methylpropyl (iso-butyl), 1-methylethyl (iso-propyl), n-butyl, and 1,1-dimethylethyl (t-butyl), and more preferably a maximum of 4 carbon atoms. The alkyl group may be unsubstituted or may be substituted with one or more substituents, preferably with one to three substituents, and most preferably with one substituent. The substituents are selected from the group consisting of hydroxy, alkoxy, amino, mono- or di-alkylamino, acetoxy, alkylcarbonyloxy, alkoxycarbonyl, carbamoyl and halogen.

The term "alkenyl" as used therein, alone or in combination, refers to a hydrocarbon chain as defined for alkyl having at least one olefinic double bond (including for example, allyl and butenyl) and having the general formula $C_mH_{2m-1}$ wherein m is an integer greater than 2, preferably m is an integer of 3 to 7, and more preferably 3 to 5.

The term "alkylene" refers to a biradical branched or unbranched hydrocarbon chain containing 1 to 5 carbon atoms, such as methylene (—$CH_2$—), ethylene, propylene, trimethylene and tetramethylene. The alkylene group may be unsubstituted or may be substituted with one or more substituents, preferably with one to three substituents, and most preferably with one substituent. The substituents are selected from the group consisting of hydroxy, alkoxy, amino, mono- or di-alkylamino, acetoxy, alkylcarbonyloxy, alkoxycarbonyl, carbamoyl and halogen.

The term "aryl" refers to an aromatic carbocyclic radical, i.e., a 6 or 10 membered aromatic or partially aromatic ring, e.g., phenyl ("Ph"), naphthyl or tetrahydronaphthyl, preferably phenyl or naphthyl, and most preferably phenyl. The aryl moiety is optionally substituted with one or more subsituents, preferably one to three, most preferably one, selected from the group consisting of halogen, preferably fluorine, chlorine, alkoxycarbonyl (e.g., methoxycarbonyl), alkylcarbonyloxy (e.g., acetoxy), cyano, alkyl, alkoxy, phenyl, phenoxy, trifluoromethyl, trifluoromethoxy, alkylthio, hydroxy, alkylcarbonylamino, heterocyclyl, sulfamoyl (i.e., $H_2NSO_2$—), amino, 1,3-dioxolyl and 1,4-dioxolyl. Especially preferred substituents are alkyl, alkoxy, hydroxy, halogen, amino, alkylamino, dialkylamino, alkylthio, sulfamoyl, benzyl or heterocyclyl.

The term "aryl(C1–C5)alkyl" refers to an alkyl group as defined above substituted with an aryl as defined above. The aryl group of the aryl(C1–C5)alkyl maybe substituted with one or more substituents, preferably one to three, most preferably with one substituent selected from the group consisting of halogen, preferably fluorine, chlorine, alkoxycarbonyl (e.g., methoxycarbonyl), alkylcarbonyloxy (e.g., acetoxy), cyano, alkyl, alkoxy, phenyl, phenoxy, trifluoromethyl, trifluoromethoxy, alkylthio, hydroxy, alkylcarbonylamino, heterocyclyl, sulfamoyl, amino, 1,3-dioxolyl and 1,4-dioxolyl. Especially preferred substituents of aryl(C1–C5)alkyl are alkoxy, hydroxy, halogen, amino, mono- or di-alkylamino or alkylthio.

The term "alkoxy" refers to the group —O—R' wherein R' is an alkyl as defined above.

The term "cycloalkyl" refers to a saturated, cyclic hydrocarbon group with 3–7 carbon atoms, preferably with 4–7 carbon atoms, more preferably 4–6 carbon atoms, i.e., cyclopropyl, cyclobutyl, cyclopentyl and cyclohexyl and the like. The cycloalkyl group may be substituted or unsubstituted. The substituents are selected from alkyl, phenyl, amino, hydroxy and halogen.

The term "cycloalkyl alkyl" refers to a branched or straight chain monovalent saturated aliphatic carbon radical of 1 to 5, preferably 1 to 3 carbon atom(s) having a monovalent carbocyclic radical of 3 to 7 carbon atoms, preferably 3 to 6 carbon atoms.

The term "aliphatic ring" refers to a monovalent carbocyclic radical of 3 to 7 carbon atoms, preferably 3 to 6 carbon atoms, such as cyclopropane, cyclobutane, cyclopentane and cyclohexane, which may contain 1 to 3 heteroatom(s), preferably 1 to 2, selected from oxygen, nitrogen and sulfur. The examples of aliphatic ring containing heteroatom(s) are morpholine ring, thiomorpholine ring, pyrrolidine ring, piperidine ring and piperazine ring.

The term "alkylthio" refers to the group $R^b$—S—, wherein $R^b$ is an alkyl group as defined above.

The term "amino" refers to the group —$NH_2$ and includes amino groups which are protected by a group known in the art such as a benzyloxycarbonyl group, acetyl group, alkoxycarbonyl group or benzyl group and the like.

The term "halogen" refers to fluoro, chloro, bromo and iodo.

The term "heteroatom" refers to oxygen, nitrogen and sulfur.

The term "hydroxy" refers to the group —OH.

The term "cyano" refers to the group —CN.

The term "mercapto" refers to the group —SH.

The term "cycloalkyl alkyloxy" means the group $R^c$—O—, wherein $R^c$ is an cycloalkyl alkyl group as defined above.

The term "alkylsulfinyl" means the group $R^d$—SO—, wherein $R^d$ is an alkyl group as defined above.

The term "alkylsulfonyl" means the group $R^e$—$SO_2$—, wherein $R^e$ is an alkyl group as defined above.

The term "halogeno alkyl" means alkyl substituted with one or more halogen atoms.

The term "alkenyloxy" means the group $R^f$—O—, wherein $R^f$ is an alkenyl group as defined above.

The term "cycloalkyloxy" means the group $R^g$—O—, wherein $R^g$ is a cycloalkyl group as defined above.

The term "mono- and di-alkylamino" refers to an amino group substituted with an alkyl group or a di-alkyl group as defined above, i.e., alkyl-NH— and dialkyl-N—.

The term "benzene ring having (C1–C5) alkylenedioxy group" preferably means benzo[1,3]dioxole and 2,3-dihydrobenzo[1,4]dioxine and most preferably benzo[1,3]dioxole.

In the present invention, the expression "optionally substituted with" means that substitution can occur at one or more positions, preferably at one to three positions, and, unless otherwise indicated, that the substituents are independently selected from the specified options.

"Pharmaceutically acceptable salt" refers to conventional acid-addition salts or base-addition salts which retain the biological effectiveness and properties of the compounds of formula [I], and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from potassium, sodium, ammonium, and quarternary ammonium hydroxide, such as, for example, tetramethylammonium hydroxide. The term "pharmaceutically acceptable salt" also comprises prodrugs of polycyclic compounds of formula [I] or corresponding salts thereof.

"Pharmaceutically acceptable," such as pharmaceutically acceptable carrier, excipient, prodrug, etc., means pharmacologically acceptable and substantially non-toxic to the subject to which the particular compound is administered.

"Pharmaceutically active metabolite" means a metabolic product of a compound of formula [I] which is pharmaceutically acceptable and effective.

The term "prodrug" refers to the compounds of the formula [I] that may be converted under physiological conditions or by solvolysis to any of the compounds of the formula [I] or to a pharmaceutically acceptable salts of the compounds of the formula [I]. A prodrug may be inactive when administered to a subject but is converted in vivo to an active compound of the formula [I].

In a preferred embodiment, the invention comprises compounds of formula [I] wherein ring A is a nitrogen-containing 5 or 6 membered heteroaromatic ring, which may be substituted by $R^1$ and $R^2$. Preferably, ring A is a pyridine, pyrazine, pyridazine or pyrimidine ring, and more preferably a pyridine ring.

In a preferred embodiment, ring B is a benzene ring, naphthalene ring or benzene ring having (C1–C5) alkylenedioxy group which is optionally substituted by $R^3$, $R^4$ and $R^5$.

In a further preferred embodiment, the invention comprises compounds of formula [I], wherein ring B is a benzene ring, naphthalene ring or benzene ring having (C1–C5) alkylenedioxy group. More preferably, ring B is a benzene ring or benzo[1,3]dioxole. Most preferably, ring B is a benzene ring.

In a preferred embodiment, the invention comprises compounds of formula [I] wherein one of $R^1$ and $R^2$ is hydrogen, (C1–C5) alkyl or —NHCH$_2$C(CH$_3$)$_2$CH$_2$N(CH$_3$)$_2$. More preferably, one of $R^1$ and $R^2$ is hydrogen, —CH$_3$ or —NHCH$_2$C(CH$_3$)$_2$CH$_2$N(CH$_3$)$_2$.

In another preferred embodiment, the present invention comprises compounds of formula [I], wherein $R^1$ is hydrogen and $R^2$ is —CH$_3$.

In another preferred embodiment, the present invention comprises compounds of formula [I], wherein $R^1$ and $R^2$ are hydrogen.

In a further preferred embodiment, the invention comprises compounds of formula [I], wherein X is O, N—OH or N—OCH$_3$.

In a further preferred embodiment, the invention comprises compounds of formula [I], wherein —Y—Z—N($R^6$)($R^7$) is —NH—CH$_2$CH$_2$—N(CH$_3$)$_2$ or —NH—CH$_2$CH$_2$-(pyrrolidin-1-yl).

In a preferred embodiment, the present invention comprises compounds of formula [I] wherein $R^3$, $R^4$ and $R^5$ are hydrogen, one is fluoro and the two others are hydrogen, one is hydroxy and the two others are hydrogen, one is OCH$_3$ and the two others are hydrogen, or one is hydrogen, one is hydroxy and the third is CH$_3$.

Most preferably, the present invention comprises polycyclic compounds of formula [I] wherein $R^3$, $R^4$ and $R^5$ are hydrogen; $R^3$, $R^4$ are hydrogen and $R^5$ is hydroxy; $R^3$, $R^4$ are hydrogen and $R^5$ is OCH$_3$; or $R^3$ is hydrogen, $R^4$ is methyl and $R^5$ is hydroxy.

Preferred polycyclic compounds in accordance with the present invention are as follows:
a) 6-(2-dimethylamino-ethylamino)-3-methoxy-5,9-diaza-benzo[c]fluoren-7-one,
b) 6-(2-dimethylamino-ethylamino)-3-hydroxy-5,9-diaza-benzo[c]fluoren-7-one,
c) 6-(2-dimethylamino-ethylamino)-5,9-diaza-benzo[c]fluoren-7-one,
d) 6-(2-dimethylamino-ethylamino)-2-fluoro-3-methoxy-5,9-diaza-benzo[c]fluoren-7-one,
e) 6-(2-dimethylamino-ethylamino)-3-hydroxy-4-methyl-5,9-diaza-benzo[c]fluoren-7-one,
f) 6-(2-dimethylamino-ethylamino)-3-ethoxy-5,9-diaza-benzo[c]fluoren-7-one,
g) 3-allyloxy-6-(2-dimethylamino-ethylamino)-5,9-diaza-benzo[c]fluoren-7-one,
h) 3-chloro-6-(2-dimethylamino-ethylamino)-5,9-diaza-benzo[c]fluoren-7-one,
i) 6-(2-dimethylamino-ethylamino)-1,3-dimethoxy-5,9-diaza-benzo[c]fluoren-7-one,
j) 6-(2-dimethylamino-ethylamino)-5,9-diaza-indeno[1,2-a]phenanthren-7-one,
k) 6-(2-dimethylamino-ethylamino)-1,3-dioxa-5,9-diaza-indeno[5,6-c]fluoren-7-one,
l) 6-(2-dimethylamino-ethylamino)-3-methoxy-5,10-diaza-benzo[c]fluoren-7-one,
m) 6-(2-dimethylamino-ethylamino)-3-hydroxy-5,10-diaza-benzo[c]fluoren-7-one,
n) 3-hydroxy-6-(2-pyrrolidin-1-yl-ethylamino)-5,10-diaza-benzo[c]fluoren-7-one,
o) 6-(2-dimethylamino-ethylamino)-3-hydroxy-4-methyl-5,10-diaza-benzo[c]fluoren-7-one,
p) 3-methoxy-4-methyl-6-(2-pyrrolidin-1-yl-ethylamino)-5,10-diaza-benzo[c]fluoren-7-one,
q) 3-hydroxy-4-methyl-6-(2-pyrrolidin-1-yl-ethylamino)-5,10-diaza-benzo[c]fluoren-7-one,
r) 3-methoxy-6-(2-pyrrolidin-1-yl-ethylamino)-5,9-diaza-benzo[c]fluoren-7-one,
s) 3-methoxy-6-(2-methylamino-ethylamino)-5,9-diaza-benzo[c]fluoren-7-one,
t) 3-methoxy-6-(4-methyl-piperazin-1-yl)-5,9-diaza-benzo[c]fluoren-7-one,
u) 3-hydroxy-6-(2-pyrrolidin-1-yl-ethylamino)-5,9-diaza-benzo[c]fluoren-7-one,
v) 3-hydroxy-6-(2-morpholin-4-yl-ethylamino)-5,9-diaza-benzo[c]fluoren-7-one,
w) 6-[(2-dimethylamino-ethyl)-methyl-amino]-3-hydroxy-5,9-diaza-benzo[c]fluoren-7-one,
x) 6-(2-dimethylamino-ethoxy)-3-hydroxy-5,9-diaza-benzo[c]fluoren-7-one,
y) 6-(2-dimethylamino-ethylamino)-3-methoxy-9-methyl-5,10-diaza-benzo[c]fluoren-7-one,
z) 6,11-bis-(2-dimethylamino-ethylamino)-3-methoxy-5,10-diaza-benzo[c]fluoren-7-one,
aa) 11-(3-dimethylamino-2,2-dimethyl-propylamino)-6-(2-dimethylamino-ethylamino)-3-methoxy-5,10-diaza-benzo[c]fluoren-7-one,
bb) 11-(3-dimethylamino-2,2-dimethyl-propylamino)-6-(2-dimethylamino-ethylamino)-3-methoxy-4-methyl-5,10-diaza-benzo[c]fluoren-7-one,
cc) 6-(2-dimethylamino-ethylamino)-3-hydroxy-9-methyl-5,10-diaza-benzo[c]fluoren-7-one,
dd) 6-(2-dimethylamino-ethylamino)-3-hydroxy-8-methyl-5,9-diaza-benzo[c]fluoren-7-one,
ee) 11-(3-dimethylamino-2,2-dimethyl-propylamino)-6-(2-dimethylamino-ethylamino)-3-hydroxy-4-methyl-5,10-diaza-benzo[c]fluoren-7-one,
ff) 6-(2-dimethylamino-ethylamino)-3-hydroxy-5,9-diaza-benzo[c]fluoren-7-one oxime,
gg) 6-(2-dimethylamino-ethylamino)-3-hydroxy-5,9-diaza-benzo[c]fluoren-7-one O-methyl-oxime and hh) 6-(2-dimethylamino-ethylamino)-3-hydroxy-4-methyl-5,9-diaza-benzo[c]fluoren-7-one O-methyl-oxime.

Further preferred polycyclic compounds in accordance with the present invention are as follows:

a) 6-(2-dimethylamino-ethylamino)-3-methoxy-5,9-diaza-benzo[c]fluoren-7-one,
b) 6-(2-dimethylamino-ethylamino)-3-hydroxy-5,9-diaza-benzo[c]fluoren-7-one,
c) 6-(2-dimethylamino-ethylamino)-5,9-diaza-benzo[c]fluoren-7-one,
d) 6-(2-dimethylamino-ethylamino)-3-hydroxy-5,10-diaza-benzo[c]fluoren-7-one,
e) 3-hydroxy-6-(2-pyrrolidin-1-yl-ethylamino)-5,10-diaza-benzo[c]fluoren-7-one,
f) 6-(2-dimethylamino-ethylamino)-3-hydroxy-4-methyl-5,10-diaza-benzo[c]fluoren-7-one,
g) 3-hydroxy-4-methyl-6-(2-pyrrolidin-1-yl-ethylamino)-5,10-diaza-benzo[c]fluoren-7-one,
h) 3-hydroxy-6-(2-pyrrolidin-1-yl-ethylamino)-5,9-diaza-benzo[c]fluoren-7-one,
i) 6-(2-dimethylamino-ethylamino)-3-hydroxy-9-methyl-5,10-diaza-benzo[c]fluoren-7-one, and
j) 11-(3-dimethylamino-2,2-dimethyl-propylamino)-6-(2-dimethylamino-ethylamino)-3-hydroxy-4-methyl-5,10-diaza-benzo[c]fluoren-7-one.

Polycyclic compounds of the formula [I] of the present invention can be produced via following methods:

A process for producing polycyclic compounds of the formula [I],

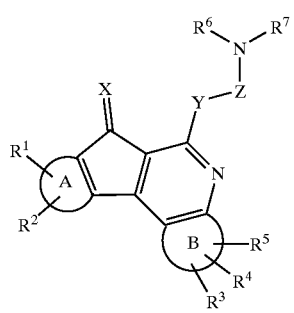

wherein ring A, ring B, $R^1$, $R^2$, $R^3$, $R^4$, $R^5$, $R^6$, $R^7$, Y and Z, are the same as defined above X is O, which comprises substitution of -Hal of a compound of the formula [VI] or $-OS(O_2)R^{12}$ of a compound of the formula [VII] by $-Y-Z-N(R^6)(R^7)$,

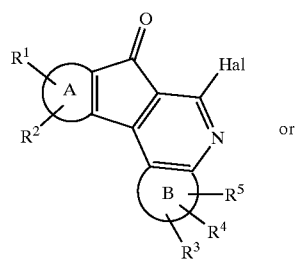

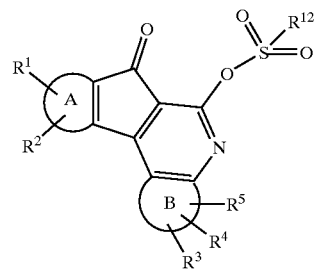

wherein ring A, ring B, $R^1$, $R^2$, $R^3$, $R^4$ and $R^5$ are the same as defined above; Hal is halogen; and $R^{12}$ is (C1–C5) alkyl, (C1–C5) halogenoalkyl or aryl, effected by reacting a compound of the formula [VI] or [VII] with a compound of the formula [VIII],

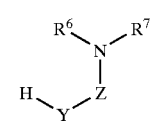

wherein $R^6$, $R^7$, Y and Z are the same as defined above.

In more detail, the compounds of the present invention can be prepared as follows:

Process 1

Key intermediates, compounds 6 and 7, can be prepared according to the following Flow Chart 1:

Flow Chart 1: Preparation of key intermediates.

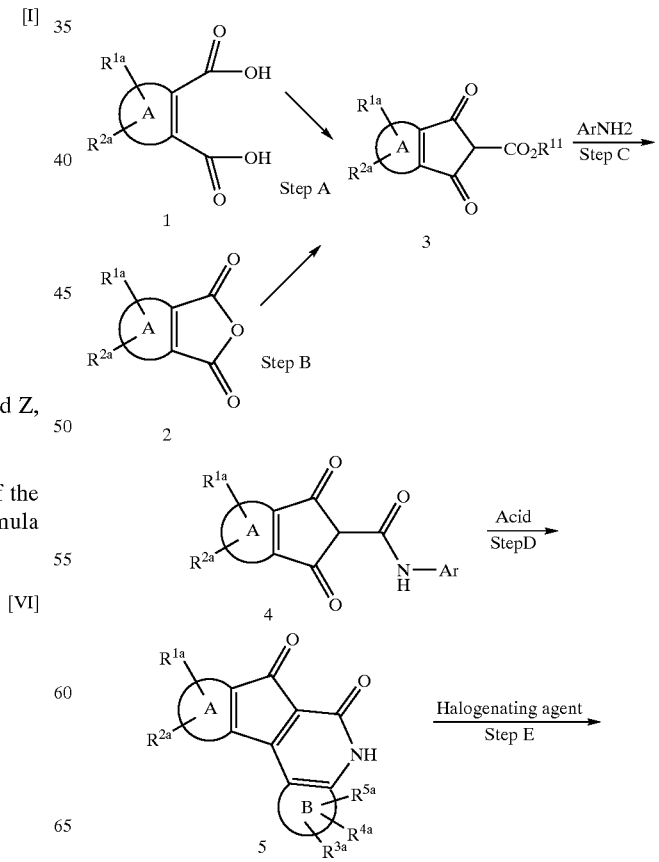

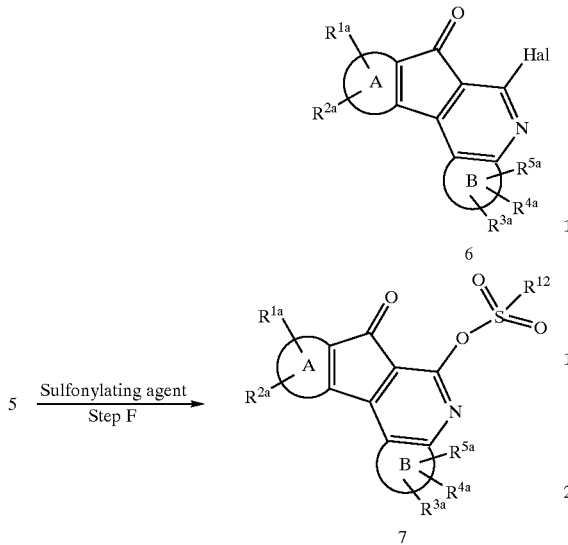

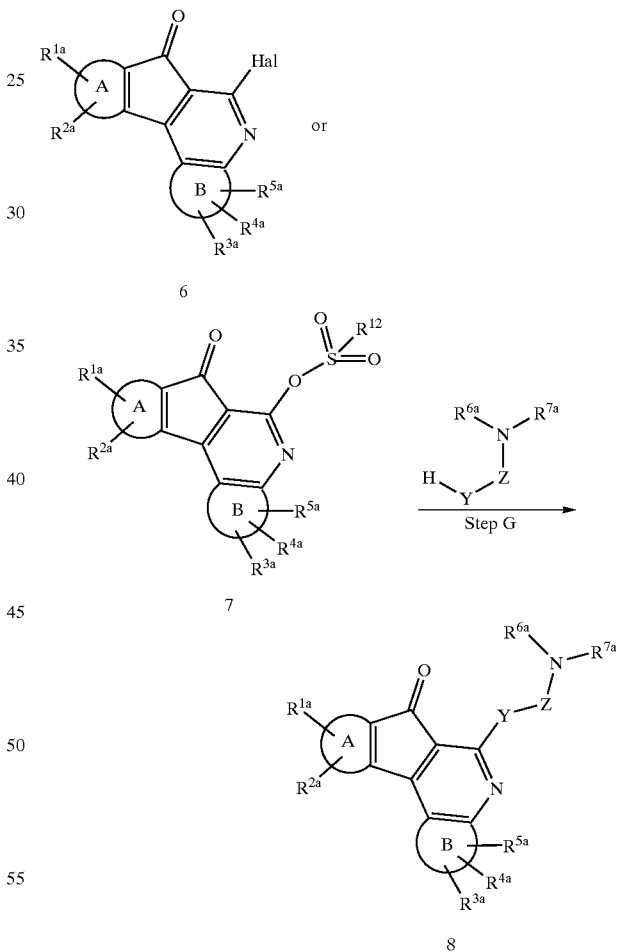

The definitions of the symbols in Flow Chart 1 are as follows. Hal is halogen. $R^{11}$ is (C1–C5) alkyl such as methyl, ethyl, propyl and butyl. $R^{1a}$ and $R^{2a}$ are $R^1$ and $R^2$, respectively, or protected $R^1$ and protected $R^2$ which can be converted to $R^1$ and $R^2$, respectively, by methods known in the art. $R^{12}$ is (C1–C5) alkyl such as methyl, (C1–C5) halogenoalkyl such as trifluoromethyl or aryl, such as p-methylphenyl and phenyl. $R^{3a}$, $R^{4a}$ and $R^{5a}$ are the same as $R^3$, $R^4$ and $R^5$ defined above, respectively; or protected $R^3$, protected $R^4$ and protected $R^5$ which can be easily converted to $R^3$, $R^4$ and $R^5$, respectively, by known methods per se. $ArNH_2$ is an aniline derivative which is optionally substituted by $R^{3a}$, $R^{4a}$ and $R^{5a}$. The definitions of ring A and ring B are the same as defined above.

For example, typically, dicarboxylic acid 1 is converted into compound 3 by 1) refluxing compound 1 in acetic anhydride and then 2) treating the resulting acid anhydride with acetoacetic acid ester in the presence of a base such as triethylamine in acetic anhydride at room temperature (see, Robin D. Allan and Joyce Fong, Aust. J. Chem., Vol. 36, Pp. 1221–1226, 1983). Compound 3 can also be prepared from dicarboxylic acid anhydride 2 by treatment with acetoacetic acid ester and a base such as triethylamine in acetic anhydride at room temperature (see, Binder D., Monatshefte fur Chemie, Vol. 105, Pp. 179–186, 1974). Compound 4 is obtained by heating compound 3 with $ArNH_2$ in an inert solvent such as toluene. The reaction temperature is from 40° C. to 160° C., preferably 80° C. to 110° C. The amide 4 can be cyclized to obtain polycyclic lactam 5 by heating compound 4 in an acid such as polyphosphoric acid, trifluoromethane sulfonic acid and sulfonic acid. The compound 5 can be halogenated by a halogenating reagent such as thionyl chloride, thionyl bromide, phosphorous oxychloride, phosphorous chloride and phosphorous bromide. The preferable temperature for this reaction ranges from room temperature to reflux, and most preferably 50° C. to 110° C. Thus, the key intermediate 6 can be synthesized. The compound 5 can be sulfonylated by treating 5 with a sulfonylating agent such as methanesulfonyl chloride, benzenesulfonyl chloride, p-toluenesulfonyl chloride and trifluoromethanesulfonic anhydride. Typically, compound 5, the sulfonylating agent and a phase transfer catalyst such as tetrabutylammonium bromide are suspended in a mixture of an organic solvent, such as dichloromethane and water containing a base such as sodium hydroxide, and the mixture is vigorously stirred for a few hours to a few days, typically overnight.

When one of $R^{1a}$, $R^{2a}$, $R^{3a}$, $R^{4a}$ and $R^{5a}$ of compound 6 is alkoxy such as methoxy. This alkoxy group can be cleaved by sulfuric acid at 160° C. to give a hydroxy derivative. The resulting phenol group can be further modified by methods known in the art. For example, when the phenol having the general formula 6 is treated with (C1–C5) alkyl halide, aryl(C1–C5)alkyl halide, (C3–C5) alkenyl halide, (C4–C7) cycloalkyl halide and (C3–C7) cycloalkyl (C1–C5) alkyl halide, (C1–C5) alkoxy, aryl (C1–C5)alkyloxy, (C3–C5) alkenyloxy, (C4–C7)cycloalkyloxy and C3–C7)cycloalkyl (C1–C5) alkyloxy derivatives can be prepared, respectively.

Active polycyclic compounds can be synthesized from the key intermediates 6 or 7 by reacting 6 or 7 with HY—Z—N($R^{6a}$)($R^{7a}$) (various amines, alcohols and thiols) as shown in Flow Chart 2. The definitions of Y and Z are the same as defined above and $R^{6a}$ and $R^{7a}$ are defined as below.

Process 2

Flow Chart 2: Modification of key intermediates.

The definitions of the symbols in Flow Chart 2 are as follows. Hal is halogen. $R^{12}$ is (C1–C5) alkyl such as methyl, (C1–C5) halogenoalkyl such as trifluoromethyl or aryl such as p-methylphenyl and phenyl. $R^{3a}$, $R^{4a}$ and $R^{5a}$ are the same as $R^3$, $R^4$ and $R^5$ defined above, respectively; or protected $R^3$, protected $R^4$ and protected $R^5$ which can be easily converted to $R^3$, $R^4$ and $R^5$, respectively, by methods known to the skilled artisan. $R^{6a}$ and $R^{7a}$ are the same as $R^6$ and $R^7$ defined above, respectively; or protected $R^6$ and protected $R^7$ which can be easily converted to $R^6$ and $R^7$, respectively, by methods known in the art. The definitions of ring A, ring B, Y and Z are the same as defined above.

When Y is $N(R^9)$ wherein $R^9$ has the same meaning defined above, the key intermediates 6 and 7 can be aminated by treatment of 6 or 7 with an amine, $HN(R^9)$—Z—$N(R^{6a})(R^{7a})$, in a solvent such as pyridine and N,N-dimethylformamide (DMF) or without solvent. The reaction temperature for this step is preferably 0° C. to 115° C., and most preferably room temperature to 100° C.

When Y is O or S, the key intermediates 6 and 7 can be reacted with 6 or 7 with HY—Z—$N(R^{6a})(R^{7a})$ in the presence of a base such as NaH in a solvent such as DMF. The reaction temperature for this step is preferably −20° C. to 50° C., and most preferably 0° C. to room temperature.

The active polycyclic compounds obtained can be further modified by the methods as shown in Flow Chart 3 and Flow Chart 4.

Process 3

Flow Chart 3: Further modification of ring A.

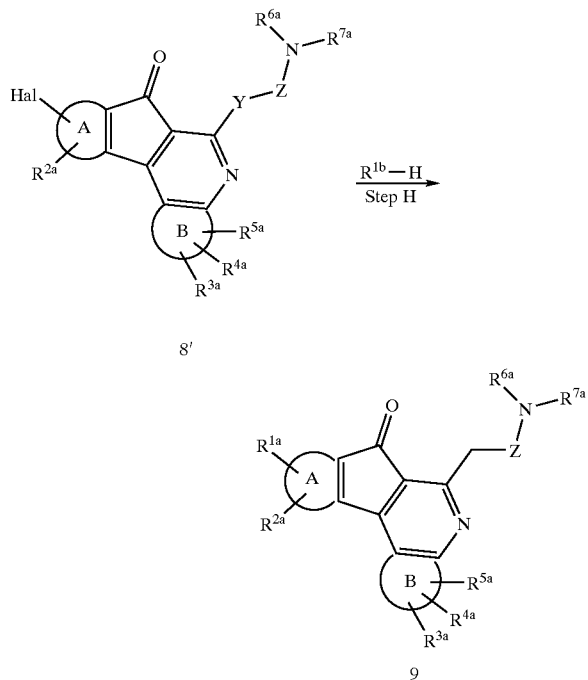

8'

9

The definitions of the symbols in Flow Chart 3 are as follows. Compound 8' is the same as compound 8 in Flow Chart 2 wherein $R^{1a}$ is halogen. Hal is halogen. $R^{1b}$ is a hydroxy, (C1–C5) alkoxy, amino, mono-(C1–C5)-alkyl-amino, di-(C1–C5)-alkyl-amino or —Y'—Z'—$N(R^{6a'})(R^{7a'})$ radical wherein Y' and Z' have the same definitions as described above; $R^{6a'}$ and $R^{7a'}$ are the same as $R^{6'}$ and $R^{7'}$, respectively, or protected $R^{6'}$ and protected $R^{7'}$ which can be converted to $R^{6'}$ and $R^{7'}$, respectively, by methods known in the art. $R^{2a}$, $R^{3a}$, $R^{4a}$ and $R^{5a}$ are the same as $R^2$, $R^3$, $R^4$ and $R^5$, respectively, or protected $R^2$, protected $R^3$, protected $R^4$ and protected $R^5$ which can be converted to $R^2$, $R^3$, $R^4$ and $R^5$, respectively, by methods known in the art. $R^{6a}$ and $R^{7a}$ are the same as $R^6$ and $R^7$, respectively, or protected $R^6$ and protected $R^7$ which can be converted to $R^6$ and $R^7$, respectively, by methods known in the art. Ring A, ring B, Y and Z have the same definitions as mentioned above.

When the alpha position of the ring nitrogen in the ring A is substituted by halogen such as Cl, this halogen can also be replaced by various substituents such as hydroxy, (C1–C5) alkoxy, amino, mono-(C1–C5)-alkylamine, di-(C1–C5)-alkylamine or —Y'—Z'—$N(R^{6a'})(R^{7a'})$ as shown in Flow Chart 3 by practically the same method as the step G in Flow Chart 2.

Process 4

The cyclopentadiene moiety of the polycyclic compounds can be further modified by the method in Flow Chart 4.

Flow Chart 4: Modification of the cyclopentadiene ring.

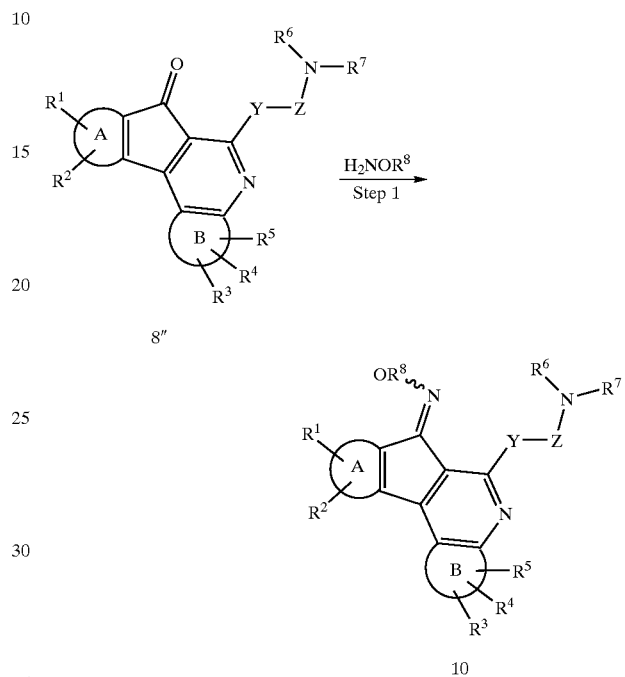

8''

10

Ring A, ring B, $R^1$, $R^2$, $R^3$, $R^4$, $R^5$, $R^6$, $R^7$, $R^8$, Y and Z have the same definitions as defined above.

The ketone group of the cyclopentadiene moiety can be modified by the reaction with oxime or various oxime-ethers ($H_2N$—O—$R^8$) in the absence or in the presence of an acid such as hydrochloric acid, hydrobromic acid and acetic acid in an appropriate solvent such as pyridine at an elevated temperature, typically at about 80° C.

Protective groups which may be used in processes 1 to 3 can typically be cleaved as follows: 1) when a phenol group is protected by methyl or benzyl ether, the protective group can be cleaved by $BBr_3$ treatment or acid hydrolysis using hydrobromic acid or sulfuric acid to give a phenol group and 2) when an amino group is protected by t-butoxycarbonyl (Boc), the protective group can be cleaved by acid such as trifluoroacetic acid to give an amino group.

The manufacture of the pharmaceutically acceptable acid addition salts of the compound of the formula [I] can be carried out by treating a free base of the compound represented by the formula [I] with an acid in a procedure known in the art for the salt formation. Examples of therapeutically acceptable acids useful in the above process are inorganic acids (e.g., hydrochloric acid, hydrobromic acid, phosphoric acid, nitric acid and sulfuric acid) and organic acids (e.g., oxalic acid, acetic acid, formic acid, trifluoroacetic acid, maleic acid, succinic acid, fumaric acid, tartaric acid, citric acid, salicylic acid, sorbic acid, lactic acid and methane-sulfonic acid). Moreover, the compounds of the formula [I] can be converted into hydrates or solvates, and their salts by various methods known to those skilled in the art.

The polycyclic compounds of the formula [I] show strong anti-tumor activity against various tumor cell lines. This anti-tumor activity indicates that the compounds of the formula [I] and pharmaceutically acceptable salts thereof can be anti-tumor agents.

The polycyclic compounds of the formula [I] and pharmaceutically acceptable salts thereof are very strong cytotoxic agents. They are active against a variety of cell lines including colon cancer cell lines, non-small cell lung cancer cell lines, pancreatic cancer cell lines and gastric cancer cell lines, etc.

Thus, the polycyclic compounds of the present invention are useful for the treatment of cancer. Accordingly, the present invention comprises the use of the above compounds for the manufacture of medicaments for the treatment of cancer and the corresponding pharmaceutical compositions, which comprise a polycyclic compound as defined above and a pharmaceutically acceptable carrier.

For example, they are useful in treating leukemia, lymphoma, myeloma, prostate cancer, breast cancer, hepatoma, glioblastoma, ovarian cancer, melanoma, lung cancer, colorectal cancer, pancreatic cancer, and gastric cancer and so on.

The anti-tumor activity of the polycyclic compounds of the present invention can be demonstrated as follows:

Determination of the Anti-tumor Activity

Anti-proliferative Activity Assay

A single suspension of tumor cells was inoculated to the serially diluted 96-well microtestplate. Then the testplate was incubated in the 5% $CO_2$ ambience at 37° C. for 4 days ($2-3 \times 10^3$ cells/well). The degree of cell growth in a monolayer was measured by using WST-8 (Dojindo, Japan). $IC_{50}$ values of the polycyclic compounds concerned against tumor cells were calculated as the concentration of drug yielding 50% OD of the control growth. The $IC_{50}$ value measures the drug concentration for 50% inhibition of the growth of tumor cells in vitro as compared to the control.

The anti-tumor activity of polycyclic compounds of the formula [I] against in vitro growth of HCT116 cell line (colorectal cancer) is summarized in Table 1.

TABLE 1

Anti-tumor activity in vitro

| Compound (ng/ml) | HCT116 (colorectal cancer) $IC_{50}$ |
|---|---|
| Example 41, | |
| 6-(2-dimethylamino-ethylamino)-3-hydroxy-5,9-diaza-benzo[c]fluoren-7-one | 0.35 |
| Example 46, | |
| 6-(2-dimethylamino-ethylamino)-3-hydroxy-4-methyl-5,9-diaza-benzo[c]fluoren-7-one | 2.2 |
| Example 45, | |
| 6-(2-dimethylamino-ethylamino)-3-hydroxy-4-methyl-5,10-diaza-benzo[c]fluoren-7-one | 3.9 |
| Example 47, | |
| 6-(2-dimethylamino-ethylamino)-3-hydroxy-9-methyl-5,10-diaza-benzo[c]fluoren-7-one | 3.9 |
| Reference compound, | |
| 6-(2-dimethylamino-ethylamino)-3-hydroxy-7H-indeno[2,1-c]quinolin-7-one | 12 |

Reference compound has been disclosed in EP 0713870 (1996) as an anti-tumor agent.

The acute toxicity ($LD_{50}$) of the polycycle compounds of the present invention was examined by intravenous administration in mice. The $LD_{50}$ value of the compounds was more than 90 mg/Kg.

For clinical use, the polycycle compounds of the formula [I], their prodrugs, or salt forms thereof and the like can be administered alone, but will generally be administered in pharmaceutical admixture formulated as appropriate to the particular use and purpose desired, by mixing excipient, binding agent, lubricant, disintegrating agent, coating material, emulsifier, suspending agent, solvent, stabilizer, absorption enhancer and/or ointment base. The admixture can be used for oral, injectable, rectal or topical administration.

In more detail, as mentioned earlier, medicaments containing a compound of formula [I] or its prodrug are also a part of the present invention, as is a process for the manufacture of such medicaments, whose process comprises bringing one or more compounds of formula [I] and, if desired, one or more other therapeutically valuable substances into a galenical administration form.

The pharmaceutical compositions may be administered orally, for example in the form of tablets, coated tablets, dragées, hard or soft gelatine capsules, solutions, emulsions or suspensions. Administration can also be carried out rectally, for example using suppositories; locally or percutaneously, for example using ointments, creams, gels or solutions; or parenterally, for example using injectable solutions.

For the preparation of tablets, coated tablets, dragées or hard gelatine capsules, the compounds of the present invention may be admixed with pharmaceutically inert, inorganic or organic excipients. Examples of suitable excipients for tablets, dragées or hard gelatine capsules include lactose, maize starch or derivatives thereof, talc or stearic acid or salts thereof.

Suitable excipients for use with soft gelatine capsules include, for example, vegetable oils, waxes, fats, semi-solid or liquid polyols, etc. According to the nature of the active ingredients, it may however be the case that no excipient is needed at all for soft gelatine capsules.

For the preparation of solutions and syrups, excipients which may be used include for example water, polyols, saccharose, invert sugar and glucose.

For injectable solutions, excipients which may be used include for example water, alcohols, polyols, glycerine, and vegetable oils.

For suppositories, and local or percutaneous application, excipients which may be used include for example natural or hardened oils, waxes, fats and semi-solid or liquid polyols.

The pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically valuable agents.

In summary, a pharmaceutical formulation for oral administration may be granule, tablet, sugar coated tablet, capsule, pill, suspension or emulsion, which for parenteral injection, for example, intravenously, intramuscularly or subcutaneously, may be used in the form of a sterile aqueous solution which may contain other substances, for example, salts or glucose to make the solution isotonic. The anti-tumor agent can also be administered in the form of a suppository or pessary, or they may be applied topically in the form of a lotion, solution, cream, ointment or dusting powder.

The daily dosage level of the polycyclic compounds of the formula [I] is from 5 to 2,000 mg/m² when administered by either the oral or parenteral route. Thus, tablets or capsules can contain from 5 mg to 1,000 mg of active compound for administration singly or two or more at a time as appropriate. In any event, the actual dosage can be determined by the weight and response of the particular patient.

The following examples illustrate the preferred methods for the preparation of the compounds of the present invention, which are not intended to limit the scope of the invention thereto.

EXAMPLE 1

Preparation of 6-(2-dimethylamino-ethylamino)-3-methoxy-5,10-diaza-benzo[c]fluoren-7-one a) Preparation of 5,7-dioxo-6,7-dihydro-5H-[2]pyrindine-6-carboxylic acid (3-methoxy-phenyl)-amide 5,7-Dioxo-6,7-dihydro-5H-[2]pyrindine-6-carboxylic acid ethyl ester (18 g) (see, Robin D. Allan and Joyce Fong, Aust. J. Chem., Vol. 36, Pp. 1221–1226, 1983), m-anisidine (17.7 ml) and acetic acid (9 ml) were suspended in toluene (1,000 ml). This mixture was refluxed for 110 minutes under nitrogen. The mixture was cooled to room temperature and the precipitate (ppt) was collected with suction. The ppt was washed with toluene and dichloromethane and dried under reduced pressure to give a brown powder (21.6 g). ESI-MS: m/z 297 (MH$^+$); $^1$H-NMR (DMSO-d6): δ3.74 (3H, s), 6.54 (1H, dd, J=8.5 Hz, J=2.5 Hz), 7.00 (1H, bd, J=8.5 Hz), 7.17 (1H, t, J=8.5 Hz), 7.42 (1H, t-like, J=ca 2.5 Hz), 7.73 (1H, d, 5 Hz), 8.71 (1H, s), 8.91 (1H, d, J=5 Hz), 10.65 (1H, brs).

b) Preparation of a mixture of 3-methoxy-5H-5,9-diaza-benzo[c]fluorene-6,7-dione and 3-methoxy-5H-5,10-diaza-benzo[c]fluorene-6,7-dione 5,7-Dioxo-6,7-dihydro-5H-[2]pyrindine-6-carboxylic acid (3-methoxy-phenyl)-amide (11 g) obtained above was triturated in polyphosphoric acid (Merck: 150 g) and the mixture was stirred at 110° C. for two hours under Ar. To the cooled mixture were added ice (400 g) and ammonia water to adjust the pH 7. Dark brown ppt was collected with suction and washed with water to give a mixture (9.85 g) of 3-methoxy-5H-5,9-diaza-benzo[c]fluorene-6,7-dione and 3-methoxy-5H-5,10-diaza-benzo[c]fluorene-6,7-dione. ESI-MS: m/z 279 (MH$^+$).

c) Preparation of 6-chloro-3-methoxy-5,10-diaza-benzo[c]fluoren-7-one (Example 1c-1) and 6-chloro-3-methoxy-5,9-diaza-benzo[c]fluoren-7-one (Example 1c-2)

The mixture of 3-methoxy-5H-5,9-diaza-benzo[c]fluorene-6,7-dione and 3-methoxy-5H-5,10-diaza-benzo[c]fluorene-6,7-dione (8.77 g) obtained above was suspended in phosphorus oxychloride (359 g) and stirred at 60° C. for three days. Excess phosphorus oxychloride was evaporated under reduced pressure. The residue was treated with ice water and saturated sodium hydrogen carbonate to adjust the pH to about 7. Black ppt was collected with suction and washed water. The ppt was purified by silica gel column chromatography developed by dichloromethane-methanol-trifluoroacetic acid (200:2:1) and by dichloromethane-methanol-trifluoroacetic acid (200:4:1). This chromatography gave two yellow bands. The first band was collected and evaporated. The residue was treated with methanol to give a less polar isomer (1.72 g), 6-chloro-3-methoxy-5,10-diaza-benzo[c]fluoren-7-one (Example 1c-1) as a yellow powder. The second band was collected and evaporated. The residue was treated with methanol to give a more polar isomer (1.86 g), 6-chloro-3-methoxy-5,9-diaza-benzo[c]-fluoren-7-one (Example 1c-2) as a yellow powder.

6-Chloro-3-methoxy-5,10-diaza-benzo[c]fluoren-7-one (Example 1c-1): ESI-MS: m/z 297 (MH$^+$); $^1$H-NMR (DMSO-d6): δ4.03 (3H, s), 7.47 (1H, dd, J=9 Hz, 2.5 Hz), 7.54 (1H, d, J=2.5 Hz), 7.74 (1H, d, J=4.5 Hz), 8.78 (1H, d, J=9 Hz), 8.96 (1H, d, 4.5 Hz), 9.73 (1H, s).

6-Chloro-3-methoxy-5,9-diaza-benzo[c]fluoren-7-one (Example 1c-2): ESI-MS: m/z 297 (MH$^+$); $^1$H-NMR (DMSO-d6): δ4.02 (3H, s), 7.51 (1H, dd, J=9 Hz, 2.5 Hz), 7.55 (1H, d, J=2.5 Hz), 8.50 (1H, d, J=4.5 Hz), 8.73 (1H, d, J=9 Hz), 8.93 (1H, s), 9.00 (1H, d, 4.5 Hz).

d) Preparation of 6-(2-dimethylamino-ethylamino)-3-methoxy-5,10-diaza-benzo[c]-fluoren-7-one 6-Chloro-3-methoxy-5,10-diaza-benzo[c]fluoren-7-one (Example 1c-1) (120 mg) was suspended in N,N-dimethylethylenediamine (50 ml) and the mixture was stirred at 55° C. for four hours under Ar. N,N-dimethylethylenediamine was evaporated and the residue was dissolved in dichloromethane. The solution was washed with water and dried over anhydrous sodium sulfate. Dichloromethane was evaporated to dryness. The residue was purified by silica gel column chromatography developed by dichloromethane-methanol-ammonia water (28%)=400:20:1 and dichloromethane-methanol-ammonia water (25%)=300:20:1. The desired product was obtained as a reddish powder. ESI-MS: m/z 349 (MH$^+$); $^1$H-NMR (CDCl$_3$): δ2.41 (6H, s), 2.72 (2H, t, J=6 Hz), 3.82 (2H, q-like, J=ca 6 Hz), 3.97 (3H, s), 7.00 (1H, dd, J=9 Hz, 2.5 Hz), 7.07 (1H, d, J=2.5 Hz), 7.34 (1H, brt, J=ca 5 Hz), 7.55 (1H, dd, J=4.5 Hz, 1 Hz), 8.05 (1H, d, J=9 Hz), 8.81 (1H, d, 4.5 Hz), 9.27 (1H, d, J=1 Hz).

EXAMPLE 2

Preparation of 6-(2-dimethylamino-ethylamino)-3-methoxy-5,9-diaza-benzo[c]fluoren-7-one In a similar manner to Example 1d, 6-(2-dimethylamino-ethylamino)-3-methoxy-5,9-diaza-benzo[c]fluoren-7-one was obtained starting from the compound of Example 1c-2 and N,N-dimethylethylenediamine. The desired product was obtained as a reddish powder. EI-MS: m/z 348 (M$^+$); $^1$H-NMR (CDCl$_3$): δ2.44 (6H, s), 2.77 (2H, t, J=6 Hz), 3.83 (2H, q-like, J=ca 6 Hz), 3.97 (3H, s), 6.98 (1H, dd, J=9 Hz, 2.5 Hz), 7.08 (1H, d, J=2.5 Hz), 7.32 (1H, brt, J=ca 5 Hz), 7.86 (1H, dd, J=4.5 Hz, 1 Hz), 8.04 (1H, d, J=9 Hz), 8.85 (1H, d, 4.5 Hz), 8.86 (1H, d, J=1 Hz).

EXAMPLE 3

Preparation of 3-methoxy-6-(2-pyrrolidin-1-yl-ethylamino)-5,10-diaza-benzo[c]fluoren-7-one In a similar manner to Example 1d, 3-methoxy-6-(2-pyrrolidin-1-yl-ethylamino)-5,10-diaza-benzo[c]fluoren-7-one was obtained starting from the compound of Example 1c-1 and 1-(2-aminoethyl)pyrrolidine. The desired product was obtained as an orange powder. EI-MS: m/z 374 (M$^+$); $^1$H-NMR (CDCl$_3$): δ1.85 (4H, m), 2.67 (4H, m), 2.84 (2H, t, J=6.5 Hz), 3.81 (2H, q-like, J=ca 6 Hz), 3.96 (3H, s), 6.95 (1H, dd, J=9 Hz, 2.5 Hz), 7.01 (1H, d, J=2.5 Hz), 7.32 (1H, brt, J=ca 5 Hz), 7.53 (1H, dd, J=4.5 Hz, 1 Hz), 7.99 (1H, d, J=9 Hz), 8.79 (1H, d, 4.5 Hz), 9.23 (1H, brs).

The following compounds described in Example 4 to Example 12 were prepared from the compound of Example 1c-2 and an appropriate amine in a similar manner to Example 1d.

EXAMPLE 4

Preparation of 6-(3-dimethylamino-propylamino)-3-methoxy-5,9-diaza-benzo[c]fluoren-7-one This compound was prepared from the compound of Example 1c-2 and N,N-dimethyl-1,3-propanediamine. The desired product was obtained as a waxy solid. ESI–MS: m/z 363 (MH$^+$); $^1$H-NMR (CDCl$_3$): δ1.89 (2H, quintet, J=7.0 Hz), 2.30 (6H, s), 2.46 (2H, t, J=7.0 Hz), 3.71 (2H, dt, J=5.5 Hz, 7.0 Hz), 3.94 (3H, s), 6.91 (1H, dd, J=9.5 Hz, 2.5 Hz), 7.00 (1H, d, J=2.5 Hz), 7.35 (1H, brt, J=5.5 Hz), 7.78 (1H, dd, J=4.5 Hz, 1 Hz), 7.94 (1H, d, J=9.5 Hz), 8.82 (1H, d, 4.5 Hz), 8.83 (1H, d, J=1 Hz).

EXAMPLE 5

Preparation of 6-(2-diethylamino-ethylamino)-3-methoxy-5,9-diaza-benzo[c]fluoren-7-one This compound was prepared from the compound of Example 1c-2 and N,N-diethyl-1,2-ethylenediamine. The desired product was obtained as a reddish powder. EI–MS: m/z 376 (M$^+$); $^1$H-NMR (CDCl$_3$): δ1.12 (6H, t, J=7 Hz), 2.64 (4H, q, J=7 hz), 2.76 (2H, t, J=6 Hz), 3.69 (2H, q-like, J=ca 6 Hz), 3.94 (3H, s), 6.91 (1H, dd, J=9 Hz, 2.5 Hz), 7.00 (1H, d, J=2.5 Hz), 7.41 (1H, brt, J=ca 5 Hz), 7.78 (1H, dd, J=4.5 Hz, 1 Hz), 7.94 (1H, d, J=9 Hz), 8.79 (1H, d, 4.5 Hz), 8.83 (1H, d, J=1 Hz).

EXAMPLE 6

Preparation of 3-methoxy-6-(2-pyrrolidin-1-yl-ethylamino)-5,9-diaza-benzo[c]fluoren-7-one This compound was prepared from the compound of Example 1c-2 and 1-(2-aminoethyl)pyrrolidine. The desired product was obtained as a red solid. EI–MS: m/z 374 (M$^+$); $^1$H-NMR (CDCl$_3$): δ1.85 (4H, m), 2.67 (4H, m), 2.85 (2H, t, J=7.0 Hz), 3.84 (2H, q-like, J=ca 6 Hz), 3.97 (3H, s), 6.98 (1H, dd, J=9 Hz, 2.5 Hz), 7.10 (1H, d, J=2.5 Hz), 7.35 (1H, brt, J=ca 5 Hz), 7.88 (1H, dd, J=5 Hz, 1 Hz), 8.06 (1H, d, J=9 Hz), 8.84 (1H, d, 5 Hz), 8.87 (1H, d, J=1 Hz).

EXAMPLE 7

Preparation of 3-methoxy-6-(2-morpholin-4-yl-ethylamino)-5,9-diaza-benzo[c]fluoren-7-one This compound was prepared from the compound of Example 1c-2 and N-(2-aminoethyl)morphline. The desired product was obtained as a red solid. EI–MS: m/z 390 (M$^+$); $^1$H-NMR (CDCl$_3$): δ2.58 (4H, m), 2.72 (2H, t, J=6.5 Hz), 3.81 (6H, m), 3.97 (3H, s), 6.99 (1H, dd, J=9 Hz, 2.5 Hz), 7.09 (1H, d, J=2.5 Hz), 7.48 (1H, brt, J=ca 5 Hz), 7.89 (1H, dd, J=4.5 Hz, 1 Hz), 8.07 (1H, d, J=9 Hz), 8.85 (1H, d, 4.5 Hz), 8.89 (1H, d, J=1 Hz).

EXAMPLE 8

Preparation of 6-[(2-dimethylamino-ethyl)-methyl-amino]-3-methoxy-5,9-diaza-benzo[c]fluoren-7-one This compound was prepared from the compound of Example 1c-2 and N,N,N'-trimethylethylenediamine. The desired product was obtained as a red paste. EI–MS: m/z 362 (M$^+$); $^1$H-NMR (CDCl$_3$): δ2.34 (6H, s), 2.72 (2H, t-like, J=ca 7 Hz), 3.27 (3H, s), 3.85 (2H, t-like J=ca 7 Hz), 3.96 (3H, s), 6.99 (1H, dd, J=9 Hz, 2.5 Hz), 7.04 (1H, d, J=2.5 Hz), 7.87 (1H, dd, J=5 Hz, 1 Hz), 8.12 (1H, d, J=9 Hz), 8.81 (1H, d, 5 Hz), 8.86 (1H, d, J=1 Hz).

EXAMPLE 9

Preparation of 3-methoxy-6-(4-methyl-piperazin-1-yl)-5,9-diaza-benzo[c]fluoren-7-one This compound was prepared from the compound of Example 1c-2 and 1-methylpiperazine. The desired product was obtained as a red solid. EI–MS: m/z 360 (M$^+$); $^1$H-NMR (CDCl$_3$): δ2.40 (3H, s), 2.69 (2H, t-like, J=ca 5 Hz), 3.75 (2H, t-like J=ca 5 Hz), 3.98 (3H, s), 7.08 (1H, dd, J=9 Hz, 2.5 Hz), 7.14 (1H, d, J=2.5 Hz), 7.93 (1H, dd, J=5 Hz, 1 Hz), 8.18 (1H, d, J=9 Hz), 8.85 (1H, d, 5 Hz), 8.89 (1H, d, J=1 hz).

EXAMPLE 10

Preparation of 6-(3-dimethylamino-2,2-dimethyl-propylamino)-3-methoxy-5,9-diaza-benzo[c]fluoren-7-one This compound was prepared from the compound of Example 1c-2 and N,N,2,2-tetramethyl-1,3-propylenediamine. The desired product was obtained as a red solid. ESI–MS: m/z 390 (MH$^+$); $^1$H-NMR (CDCl$_3$): δ1.04 (6H, s), 2.33 (2H, s), 2.41 (6H, s), 3.61 (2H, d, J=5 Hz), 3.96 (3H, s), 6.93 (1H, dd, J=9 Hz, 2.5 Hz), 7.06 (1H, d, J=2.5 hz), 7.85 (1H, dd, J=5 Hz, 1 Hz), 8.01 (1H, d, J=9 Hz), 8.29 (1H, brt, J=5 Hz), 8.82 (1H, d, 5 Hz), 8.86 (1H, d, J=1 Hz).

EXAMPLE 11

Preparation of 6-[2-(2-hydroxy-ethylamino)-ethylamino]-3-methoxy-5,9-diaza-benzo[c]fluoren-7-one This compound was prepared from the compound of Example 1c-2 and 2-(2-aminoethylamino)ethanol. The desired product was obtained as a reddish powder. ESI–MS: m/z 365 (MH$^+$); $^1$H-NMR (MeOH-d4): δ3.08 (2H, t, J=5.5 Hz), 3.21 (2H, m), 3.72 (2H, t, J=5.5 Hz), 3.80 (2H, m), 3.84 (3H, s), 6.90 (1H, dd, J=9 Hz, 2.5 Hz), 7.03 (1H, d, J=2.5 Hz), 7.95 (1H, d, J=5 Hz), 8.03 (1H, d, J=9 Hz), 8.59 (1H, s), 8.65 (1H, d, J=5 Hz).

EXAMPLE 12

Preparation of 3-methoxy-6-(2-methylamino-ethylamino)-5,9-diaza-benzo[c]fluoren-7-one This compound was prepared from the compound of Example 1c-2 and N-methylethylenediamine. The desired product was obtained as a red solid. EI–MS: m/z 334 (M$^+$); $^1$H-NMR (CDCl$_3$): δ2.51 (3H, s), 2.94 (2H, t, J=6 Hz), 3.82 (2H, d, J=6 Hz), 3.97 (3H, s), 6.98 (1H, dd, J=9 Hz, 2.5 Hz), 7.10 (1H, d, J=2.5 Hz), 7.88 (1H, dd, J=5 Hz, 1 Hz), 8.05 (1H, d, J=9 Hz), 8.84 (1H, d, 5 Hz), 8.87 (1H, d, J=1 Hz).

EXAMPLE 13

Preparation of 3-methoxy-6-[(piperidin-2-ylmethyl)-amino]-5,9-diaza-benzo[c]fluoren-7-one a) Preparation of 2-[(3-methoxy-7-oxo-7H-5,9-diaza-benzo[c]fluoren-6-ylamino)methyl]-piperidine-1-carboxylic acid tert-butyl ester This compound was prepared from the compound of Example 1c-2 and 2-(aminomethyl)-1-N-Boc-piperidine. The desired product was obtained as a red waxy solid. ESI–MS: m/z 475 (MH$^+$); $^1$H-NMR (CDCl$_3$): δ1.39 (9H, s), ca 1.7 (6H, m), 2.99 (1H, m), 3.75 (1H, m), 3.90 (3H, s), 4.05 (2H, br), ca 4.6 (1H, br), 6.95 (1H, dd, J=9 Hz, 2.5 Hz), 7.04 (1H, d, J=2.5 Hz), 7.06 (1H, br), 7.83 (1H, dd, J=5 Hz, 1 Hz), 7.99 (1H, d, J=9 Hz), 8.80 (1H, d, 5 Hz), 8.83 (1H, d, J=1 Hz).

b) Preparation of 3-methoxy-6-[(piperidin-2-ylmethyl)-amino]-5,9-diaza-benzo[c]-fluoren-7-one 2-[(3-Methoxy-7-oxo-7H-5,9-diaza-benzo[c]fluoren-6-ylamino)-methyl]-piperidine-1-carboxylic acid tert-butyl ester (45 mg) obtained above was stirred in a mixture of dichloromethane (1 ml) and trifluoroacetic acid (1 ml) for 85 minutes. The mixture was diluted with dichloromethane and washed with sodium hydrogen carbonate solution and water. The organic layer was dried over anhydrous sodium sulfate and evaporated to give a reddish solid (32 mg). ESI–MS: m/z 375 (MH$^+$); $^1$H-NMR (CDCl$_3$): δ1.2–1.7 (4H, m), ca 1.85 (2H, m), ca 2.4 (1H, br), ca 2.65 (1H, m), ca 2.9 (1H, m), 3.16 (1H, m), ca 3.65 (2H, m), 3.95 (3H, s), 6.92 (1H, dd, J=9 Hz, 2.5 Hz), 7.02 (1H, d, J=2.5 Hz), 7.21 (1H, brt, J=5.5 Hz)), 7.76 (1H, dd, J=5 Hz, 1 Hz), 7.93 (1H, d, J=9 Hz), 8.79 (1H, d, 5 Hz), 8.82 (1H, d, J=1 Hz).

EXAMPLE 14

Preparation of 6-(2-dimethylamino-ethylamino)-3-methoxy-5,11-diaza-benzo[c]fluoren-7-one a) Preparation of 5,7-dioxo-6,7-dihydro-5H-[1]pyrindine-6-carboxylic acid (3-methoxy-phenyl)-amide 5,7-Dioxo-6,7-dihydro-5H-[1]pyrindine-6-carboxylic acid ethyl ester (100 mg) (see D. Binder, Monatshefte für Chemie, Vol. 105, Pp. 179–186, 1974), m-anisidine (0.124 ml) and acetic acid (0.052 ml) were suspended in toluene (5 ml). This mixture was refluxed for 2 hours under nitrogen. The mixture was cooled to room temperature and the ppt was collected with suction. The ppt was washed with toluene and dichloromethane and dried under reduced pressure to give a brown powder (112 mg). ESI–MS: m/z 297 (MH$^+$); $^1$H-NMR (DMSO-d6): δ3.74 (3H, s), 6.54 (1H, dd, J=8.5 Hz, J=2.5 Hz), 7.04 (1H, bd, J=8.5 Hz), 7.16 (1H, t, J=8.5 Hz), 7.38 (1H, dd, J=7.0 Hz, 4.5 Hz), 7.44 (1H, t-like, 2.5 Hz), 7.70 (1H, dd, J=7.0 Hz, 1.5 Hz), 8.57 (1H, dd, J=4.5 Hz, 1.5 Hz), 10.79 (1H, s).

b) Preparation of a mixture of 3-methoxy-5H-5,8-diazabenzo[c]fluorene-6,7-dione and 3-methoxy-5H-5,11-diazabenzo[c]fluorene-6,7-dione 5,7-Dioxo-6,7-dihydro-5H-[1]pyrindine-6-carboxylic acid (3-methoxy-phenyl)amide (87 mg) obtained above was triturated in polyphosphoric acid (Merck: 2.5 g) and the mixture was stirred at 120° C. for two hours under Ar. To the cooled mixture was added ice water (25 ml) and sodium hydrogen carbonate solution to adjust the pH 7. Dark brown ppt was collected with suction and washed with water to give a mixture (51 mg) of 3-methoxy-5H-5,8-diaza-benzo[c]fluorene-6,7-dione and 3-methoxy-5H-5,11-diaza-benzo[c]fluorene-6,7-dione. ESI–MS: m/z 279 (MH$^+$).

c) Preparation of 6-chloro-3-methoxy-5,11-diaza-benzo[c] fluoren-7-one (Example 14c-1) and 6-chloro-3-methoxy-5,8-diaza-benzo[c]fluoren-7-one (Example 14c-2)

The mixture of 4-methoxy-5H-5,8-diaza-benzo[c]fluorene-6,7-dione and 4-methoxy-5H-5,11-diaza-benzo[c]fluorene-6,7-dione (54 mg) obtained above and DMF (0.1 ml) were suspended in phosphorus oxychloride (2 ml) and refluxed for three hours. Excess phosphorus oxychloride was evaporated under reduced pressure. The residue was treated with water and saturated sodium hydrogen carbonate to adjust the pH about 7. Orange ppt was collected with suction and washed water. The ppt was purified by silica gel column chromatography developed by dichloromethane-methanol (200:1) and by dichloromethane-methanol (200:2). This chromatography gave two yellow bands. The first band was collected and evaporated to give the less polar isomer (11.3 mg), 6-chloro-3-methoxy-5,11-diaza-benzo[c] fluoren-7-one (Example 14c-1) as a yellow powder. The second band was collected and evaporated to give the more polar isomer (20.3 mg), 6-chloro-3-methoxy-5,8-diaza-benzo[c]fluoren-7-one (Example 14c-2) as a yellow powder.

6-Chloro-3-methoxy-5,11-diaza-benzo[c]fluoren-7-one (Example 14c-1): ESI–MS: m/z 297 (MH$^+$); $^1$H-NMR (CDCl3-MeOH-d4=2:1): δ4.04 (3H, s), ca 7.4 (2H, m), 7.48 (1H, dd, J=7.0 Hz, 5.0 Hz), 8.06 (1H, dd, J=7.0 Hz, 2.0 Hz), 8.84 (1H, dd, J=7.0 Hz, 2.0 Hz), 9.34 (1H, m).

6-Chloro-3-methoxy-5,8-diaza-benzo[c]fluoren-7-one (Example 14c-2): ESI–MS: m/z 297 (MH$^+$); $^1$H-NMR ((CDCl3-MeOH-d4=2:1): δ4.05 (3H, s), ca 7.45 (2H, m), 7.63 (1H, dd, J=8.0 Hz, 5.0 Hz), 8.41 (1H, m), 8.61 (1H, dd, J=8.0 Hz, 2.0 Hz), 8.77 (1H, dd, J=5.0 Hz, 2.0 Hz).

d) Preparation of 6-(2-dimethylamino-ethylamino)-3-methoxy-5,11-diaza-benzo[c]fluoren-7-one In a similar manner to Example 1-d, the desired product was prepared starting from 6-chloro-3-methoxy-5,11-diazabenzo[c]fluoren-7-one (Example 14c-1) and N,N-dimethylethylenediamine. The product was obtained as an orange solid. ESI–MS: m/z 349 (MH$^+$); $^1$H-NMR (CDCl$_3$): δ2.37 (6H, s), 2.67 (2H, t, J=6.5 Hz), 3.79 (2H, dt, J=5.5 Hz, 6.5 Hz), 3.96 (3H, s), 6.96 (1H, dd, J=9 Hz, 2.5 Hz), 7.04 (1H, d, J=2.5 Hz), 7.25 (1H, brt, J=ca 5.5 Hz), 7.28 (1H, dd, J=4.5 Hz, 7.5 Hz), 7.85 (1H, dd, J=7.5 Hz, 1.5 Hz), 8.67 (1H, dd, 4.5 Hz, 1.5 Hz), 8.96 (1H, d, J=9 Hz).

EXAMPLE 15

Preparation of 6-(2-dimethylamino-ethylamino)-3-methoxy-5,8-diaza-benzo[c]fluoren-7-one In a similar manner to Example 1d, 6-(2-dimethylamino-ethylamino)-3-methoxy-5,8-diaza-benzo[c]fluoren-7-one was obtained starting from the compound of Example 14c-2 and N,N-dimethylethylenediamine. The desired product was obtained as an orange solid. ESI–MS: m/z 349 (MH$^+$); $^1$H-NMR (CDCl$_3$): δ2.37 (6H, s), 2.68 (2H, t, J=6.5 Hz), 3.81 (2H, dt, J=5.5 Hz, 6.5 Hz), 3.97 (3H, s), 6.95 (1H, dd, J=9 Hz, 2.5 Hz), 7.06 (1H, d, J=2.5 Hz), 7.32 (1H, brt, J=ca 5.5 Hz), 7.37 (1H, dd, J=5.0 Hz, 8.0 Hz), 7.99 (1H, d, J=9.0 Hz), 8.25 (1H, dd, 8.0 Hz, 1.5 Hz), 8.67 (1H, d, J=1.5 Hz).

EXAMPLE 16

Preparation of 6-(2-dimethylamino-ethylamino)-2-fluoro-3-methoxy-5,9-diaza-benzo[c]fluoren-7-one a) Preparation of 6-chloro-2-fluoro-3-methoxy-5,9-diaza-benzo[c]fluoren-7-one In a similar manner to Examples 1a–1c, 6-chloro-2-fluoro-3-methoxy-5,9-diaza-benzo[c]fluoren-7-one was obtained starting from 5,7-dioxo-6,7-dihydro-5H-[2] pyrindine-6-carboxylic acid ethyl ester (see Robin D. Allan and Joyce Fong, Aust. J. Chem., Vol. 36, Pp. 1221–1226, 1983) and 4-fluoro-3-methoxyaniline. The desired product was obtained as a brown powder. ESI–MS: m/z 315 (MH$^+$); $^1$H-NMR (CDCl$_3$): δ4.11 (3H, s), 7.58 (1H, d, J=8 Hz), 8.01 (1H, d, J=5 Hz), 8.05 (1H, d, J=11 Hz), 9.01 (1H, brs), 9.06 (1H, brs).

b) Preparation of 6-(2-dimethylamino-ethylamino)-2-fluoro-3-methoxy-5,9-diaza-benzo[c]fluoren-7-one This compound was prepared from 6-chloro-2-fluoro-3-methoxy-5,9-diaza-benzo[c]fluoren-7-one obtained above and N,N-dimethylethylenediamine in a similar manner to Example 1d. The desired product was obtained as a reddish powder. ESI–MS: m/z 375 (MH$^+$); $^1$H-NMR (CDCl$_3$): δ2.36 (6H, s), 2.65 (2H, t, J=6 Hz), 3.76 (2H, quartet like, J=ca 6 Hz), 4.05 (3H, s), 7.16 (1H, d, J=8 Hz), 7.31 (1H, brt, J=ca 5 Hz), 7.74 (1H, d, J=11.5 Hz), 7.80 (1H, dd, J=5 Hz, 1 Hz), 8.86 (1H, d, J=5 Hz), 8.87 (1H, d, J=1 Hz).

EXAMPLE 17

Preparation of 6-(2-dimethylamino-ethylamino)-1,3-dimethoxy-5,9-diaza-benzo[c]fluoren-7-one a) Preparation of 6-chloro-1,3-dimethoxy-5,9-diaza-benzo[c]fluoren-7-one In a similar manner to Examples 1a–1c, 6-chloro-1,3-dimethoxy-5,9-diaza-benzo[c]fluoren-7-one was obtained starting from 5,7-dioxo-6,7-dihydro-5H-[2]pyrindine-6-carboxylic acid ethyl ester (see Robin D. Allan and Joyce Fong, Aust. J. Chem., Vol. 36, Pp. 1221–1226, 1983) and 3,5-dimethoxyaniline. The desired product was obtained as a brown powder. ESI–MS: m/z 327 (MH$^+$); $^1$H-NMR (CDCl$_3$): δ4.01 (3H, s), 4.14 (3H, s), 6.72 (1H, d, J=2 Hz,), 7.10 (1H, d, J=2 Hz), 8.54 (1H, d, J=5.5 Hz), 8.96 (1H, brs), 8.99 (1H, d, J=5.5 Hz).

b) Preparation of 6-(2-dimethylamino-ethylamino)-1,3-dimethoxy-5,9-diaza-benzo[c]fluoren-7-one This compound was prepared from 6-chloro-1,3-dimethoxy-5,9-diaza-benzo[c]-fluoren-7-one obtained above and N,N-dimethylethylenediamine in a similar manner to Example 1d. The desired product was obtained as a reddish powder. ESI–MS: m/z 379 (MH$^+$); $^1$H-NMR (CDCl$_3$): δ2.34 (6H, s), 2.63 (2H, t, J=6 Hz), 3.75 (2H, quartet like, J=ca 6 Hz), 3.94 (3H, s), 4.02 (3H, s), 6.28 (1H, d, J=2 Hz,), 6.71 (1H, d, J=2 Hz), 7.62 (1H, brt, J=ca 6 Hz), 8.17 (1H, dd, J=5 Hz, 1 Hz), 8.77 (1H, d, J=5 H), 8.80 (1H, d, J=1 Hz).

EXAMPLE 18

Preparation of 6-(2-dimethylamino-ethylamino)-3-methoxy-4-methyl-5,10-diaza-benzo[c]fluoren-7-one a) Preparation of 5,7-dioxo-6,7-dihydro-5H-[2]pyrindine-6-carboxylic acid (3-methoxy-4-methyl-phenyl)-amide 5,7-Dioxo-6,7-dihydro-5H-[2]pyrindine-6-carboxylic acid ethyl ester (975 mg) (see Robin D. Allan and Joyce Fong, Aust. J. Chem., Vol. 36, Pp. 1221–1226,1983), 3-metoxy-2-methyl-phenylamine (750 mg) and acetic acid (0.4 ml) were suspended in toluene (30 ml). This mixture was refluxed for one hour under nitrogen. The mixture was cooled to room temperature and the ppt was collected with suction. The ppt was washed with toluene and dichloromethane and dried under reduced pressure to give an orange powder (1.1 g). ESI–MS: m/z 311 (MH$^+$); $^1$H-NMR (DMSO-d6+triethylamine (1 eq.)): δ2.18 (3H, s), 3.77 (3H, s), 6.60 (1H, d, J=8 Hz), 7.05 (1H, t, J=8 Hz), 7.32 (1H, dd, J=4.5 Hz, J=1 Hz), 7.99 (1H, d, J=8 Hz), 8.50 (1H, d, J=1 Hz), 8.71 (1H, d, J=4.5 Hz), 10.6 (1H, s).

b) Preparation of a mixture of 3-methoxy-4-methyl-5H-5,10-diaza-benzo[c]fluorene-6,7-dione and 3-methoxy-4-methyl-5H-5,9-diaza-benzo[c]fluorene-6,7-dione 5,7-Dioxo-6,7-dihydro-5H-[2]pyrindine-6-carboxylic acid (3-methoxy-4-methylphenyl)-amide (1 g) obtained above was triturated in polyphosphoric acid (Merck: 10 g) and the mixture was stirred at 120° C. for two hours under Ar. To the cooled mixture was added ice (400 g) and ammonia water to adjust the pH 7. Dark brown ppt was collected with suction and washed with water to give a mixture (860 mg) of 3-methoxy-4-methyl-5H-5,10-diaza-benzo[c]fluorene-6,7-dione and 3-methoxy-4-methyl-5H-5,9-diaza-benzo[c]fluorene-6,7-dione. ESI–MS: m/z 293 (MH$^+$).

c) Preparation of toluene-4-sulfonic acid 3-methoxy-4-methyl-7-oxo-7H-5,10-diaza-benzo[c]fluoren-6-yl ester (Example 18c-1) and toluene-4-sulfonic acid 3-methoxy-4-methyl-7-oxo-7H-5,9-diaza-benzo[c]fluoren-6-yl ester (Example 18c-2)

A mixture of the mixture of 3-methoxy-4-methyl-5H-5,10-diaza-benzo[c]fluorene-6,7-dione and 3-methoxy-4-methyl-5H-5,9-diaza-benzo[c]fluorene-6,7-dione (688 mg) obtained above, p-toluenesulfonyl chloride (718 mg), tetrabutylammonium bromide (1.38 g), 0.025 mol sodium hydroxide solution (140 ml), and dichloromethane (280 ml) was stirred vigorously at room temperature for 22 hours. The organic layer was separated and the water layer was extracted with dichloromethane (80 ml). The organic layer combined was evaporated under reduced pressure. The residue was titrated with methanol (150 ml) to give brown powder. The powder was purified by silica gel column chromatography developed by dichloromethane-methanol-trifluoroacetic acid (300:1). This chromatography gave two yellow bands. The first band was collected and evaporated. The residue was treated with methanol to give less polar isomer (300 mg), toluene-4-sulfonic acid 3-methoxy-4-methyl-7-oxo-7H-5,10-diaza-benzo[c]fluoren-6-yl ester (Example 18c-1) as a yellow powder. The second band was collected and evaporated. The residue was treated with methanol to give more polar isomer (250 mg), toluene-4-sulfonic acid 3-methoxy-4-methyl-7-oxo-7H-5,9-diaza-benzo[c]fluoren-6-yl ester (Example 18c-2) as a yellow powder.

Toluene-4-sulfonic acid 3-methoxy-4-methyl-7-oxo-7H-5,10-diaza-benzo[c]fluoren-6-yl ester (Example 18c-1): ESI–MS: m/z 447 (MH$^+$); $^1$H-NMR (CDCl$_3$): δ2.40 (3H, s), 2.47 (3H, s), 4.06 (3H, s), 7.39 (2H, d, J=8.5 Hz), 7.47 (1H, d, J=9 Hz), 7.66 (1H, dd, J=4.5 Hz, 1 Hz), 8.09 (2H, d, J=8.5 Hz), 8.32 (1H, d, J=9 Hz), 8.90 (1H, d, J=4.5 Hz), 9.42 (1H, d, J=1 Hz).

Toluene-4-sulfonic acid 3-methoxy-4-methyl-7-oxo-7H-5,9-diaza-benzo[c]fluoren-6-yl ester (Example 18c-2): ESI–MS: m/z 447 (MH$^+$); $^1$H-NMR (CDCl$_3$): δ2.43 (3H, s), 2.48 (3H, s), 4.06 (3H, s), 7.40 (2H, d, J=8.5 Hz), 7.46 (1H, d, J=9.5 Hz), 7.98 (1H, dd, J=5 Hz, 1 Hz), 8.09 (2H, d, J=8.5 Hz), 8.32 (1H, d, J=9.5 Hz), 8.93 (1H, d, J=5 Hz), 8.99 (1H, d, J=1 Hz).

d) Preparation of 6-(2-dimethylamino-ethylamino)-3-methoxy-4-methyl-5,10-diaza-benzo[c]fluoren-7-one Toluene-4-sulfonic acid 3-methoxy-4-methyl-7-oxo-7H-5,10-diaza-benzo[c]fluoren-6-yl ester (Example 18c-1) (25 mg) was suspended in N,N-dimethylethylenediamine (0.5 ml) and the mixture was stirred at 80° C. for one hour. The mixture was diluted with dichloromethane and washed with saturated ammonium chloride solution and water. The organic layer was dried over anhydrous sodium sulfate and evaporated to dryness. The residue was purified by silica gel column chromatography developed by dichloromethane-methanol=50:1 and dichloromethane-methanol=10:1. The desired product was obtained as a reddish powder (21 mg). ESI–MS: m/z 363 (MH$^+$); $^1$H-NMR (CDCl$_3$): δ2.36 (6H, s), 2.51 (3H, s), 2.66 (2H, t, J=6.5 Hz), 3.82 (2H, quartet like, J=ca 6.5 Hz), 4.02 (3H, s), 7.12 (1H, d, J=9 Hz,), 7.18 (1H, brt, J=ca 5.5 Hz), 7.54 (1H, dd, J=4.5 Hz, 1 Hz), 8.05 (1H, d, J=9 Hz), 8.80 (1H, d, J=4.5 Hz), 9.27 (1H, d, J=1 Hz).

EXAMPLE 19

Preparation of 6-(2-dimethylamino-ethylamino)-3-methoxy-4-methyl-5,9-diaza-benzo[c]fluoren-7-one In a similar manner to Example 18d, 6-(2-dimethylamino-ethylamino)-3-methoxy-4-methyl-5,9-diaza-benzo[c]

fluoren-7-one was obtained starting from the compound of Example 18c-2 and N,N-dimethylethylenediamine. The desired product was obtained as a reddish powder. ESI–MS: m/z 363 (MH$^+$); $^1$H-NMR (CDCl$_3$): δ2.35 (6H, s), 2.52 (3H, s), 2.66 (2H, t, J=6.5 Hz), 3.81 (2H, quartet like, J=ca 6.5 Hz), 4.01 (3H, s), 7.11 (1H, d, J=9 Hz), 7.20 (1H, brt, J=ca 6 Hz), 7.88 (1H, dd, J=5 Hz, 1 Hz), 8.05 (1H, d, J=9 Hz), 8.84 (1H, d, J=5 Hz), 8.85 (1H, d, J=1 Hz).

EXAMPLE 20

Preparation of 6-(2-dimethylamino-ethylamino)-1,2,3-trimethoxy-5,9-diaza-benzo[c]fluoren-7-one a) Preparation of toluene-4-sulfonic acid 1,2,3-trimethoxy-7-oxo-7H-5,9-diaza-benzo[c]fluoren-6-yl ester In a similar manner to Examples 18a–18c, toluene-4-sulfonic acid 1,2,3-trimethoxy-7-oxo-7H-5,9-diaza-benzo[c]fluoren-6-yl ester was obtained starting from 5,7-dioxo-6,7-dihydro-5H-[2]pyrindine-6-carboxylic acid ethyl ester (see Robin D. Allan and Joyce Fong, Aust. J. Chem., Vol. 36, Pp. 1221–1226, 1983) and 3,4,5-trimetoxy aniline. The desired product was obtained as an orange powder. ESI–MS: m/z 493 (MH$^+$); $^1$H-NMR (CDCl$_3$): δ2.50 (3H, s), 3.95 (3H, s), 4.07 (3H, s), 4.08 (3H, s), 7.27 (1H, s), 7.43 (2H, d, J=8 Hz), 8.13 (2H, d, J=8 Hz), 8.46 (1H, dd, J=5 Hz, 1 Hz), 8.90 (1H, d, J=5 Hz), 8.94 (1H, d, J=1 Hz).

b) Preparation of 6-(2-dimethylamino-ethylamino)-1,2,3-trimethoxy-5,9-diaza-benzo[c]fluoren-7-one This desired compound was prepared from toluene-4-sulfonic acid 1,2,3-trimethoxy-7-oxo-7H-5,9-diaza-benzo[c]fluoren-6-yl ester obtained above and N,N-dimethylethylenediamine in a similar manner to Example 18d. The desired product was obtained as a reddish powder. ESI–MS: m/z 409 (MH$^+$); $^1$H-NMR (CDCl$_3$): δ2.36 (6H, s), 2.64 (2H, t, J=6 Hz), 3.76 (2H, quartet like, J=ca 6 Hz), 3.90 (3H, s), 4.00 (3H, s), 4.02 (3H, s), 6.94 (1H, s), 7.55 (1H, brt, J=ca 6 Hz), 8.38 (1H, dd, J=5 Hz, 1 Hz), 8.82 (1H, d, J=5 Hz), 8.83 (1H, s).

EXAMPLE 21

Preparation of 6-(2-dimethylamino-ethylamino)-5,9-diaza-indeno[1,2-a]phenanthren-7-one a) Preparation of 5,7-dioxo-6,7-dihydro-5H-[2]pyrindine-6-carboxylic acid naphthalen-1-ylamide In a similar manner to Example 1a, 5,7-dioxo-6,7-dihydro-5H-[2]pyrindine-6-carboxylic acid naphthalen-1-ylamide was obtained starting from 5,7-Dioxo-6,7-dihydro-5H-[2]pyrindine-6-carboxylic acid ethyl ester and naphthalen-1-ylamine. The desired product was obtained as a light brownish powder. ESI–MS: m/z 317 (MH$^+$); $^1$H-NMR (DMSO-d6): δ7.38–7.67 (5H, m), 7.91 (1H, d, J=8.1 Hz), 8.38 (1H, d, J=8.7 Hz), 8.54 (1H, dd, J=1.1 Hz, 7.6 Hz), 8.57 (1H, d, J=1.1 Hz), 8.75 (1H, d, J=4.9 Hz), 11.61 (1H, brs).

b) Preparation of a mixture of 5H-5,9-diaza-indeno[1,2-a]phenanthrene-6,7-dione and 5H-5,10-diaza-indeno[1,2-a]phenanthrene-6,7-dione In a similar manner to Example 1b, a mixture of 5H-5,9-diaza-indeno[1,2-a]phenanthrene-6,7-dione and 5H-5,10-diaza-indeno[1,2-a]phenanthrene-6,7-dione was obtained starting from the compound of Example 21a as a dark brown solid. ESI–MS: m/z 299 (MH$^+$).

c) Preparation of toluene-4-sulfonic acid 7-oxo-7H-5,9-diaza-indeno[1,2-a]phenanthren-6-yl ester In a similar manner to Example 18c, toluene-4-sulfonic acid 7-oxo-7H-5,9-diaza-indeno[1,2-a]phenanthren-6-yl ester was obtained as an yellow powder starting from the compound of Example 21b. ESI–MS: m/z 453 (MH$^+$); $^1$H-NMR (DMSO-d6): δ7.59 (2H, d, J=8.6 Hz), 7.75–7.93 (2H, m), 8.06 (2H, d, J=8.6 Hz), 8.17 (1H, d, J=7.6 Hz), 8.21 (1H, d, J=9.2 Hz), 8.42 (1H, d, J=5.6 Hz), 8.61 (1H, d, J=4.9 Hz), 8.64 (1H, d, J=9.2 Hz), 8.99 (1H, s), 9.04 (1H, d, J=4.9 Hz). In DMSO-d6, the peak of methyl overlapped with that of the solvent.

d) Preparation of 6-(2-dimethylamino-ethylamino)-5,9-diaza-indeno[1,2-a]phenanthren-7-one In a similar manner to Example 18d, 6-(2-dimethylamino-ethylamino)-5,9-diaza-indeno[1,2-a]phenanthren-7-one was obtained starting from the compound of Example 21c and N,N-dimethylethylenediamine. The desired product was obtained as a reddish powder. ESI–MS: m/z 369 (MH$^+$); $^1$H-NMR (CDCl$_3$): δ2.41 (6H, s), 2.74 (2H, t, J=6.3 Hz), 3.95 (2H, q-like J=6.3 Hz), 7.42 (1H, brt, J=6.3 Hz), 7.58–7.84 (4H, m), 7.95 (1H, d, J=4.9 Hz), 8.01 (1H, d, J=8.9 Hz), 8.85 (1H, d, J=4.9 Hz), 8.90 (1H, d, J=0.7 Hz), 9.13 (1H, d, J=7.9 Hz).

EXAMPLE 22

Preparation of 6-(2-dimethylamino-ethylamino)-1,3-dioxa-5,9-diaza-indeno[5,6-c]fluoren-7-one a) Preparation of toluene-4-sulfonic acid 7-oxo-7H-1,3-dioxa-5,9-diaza-indeno[5,6-c]fluoren-6-yl ester In a similar manner to Examples 18a–18c, toluene-4-sulfonic acid 7-oxo-7H-1,3-dioxa-5,9-diaza-indeno[5,6-c]fluoren-6-yl ester was obtained starting from 5,7-dioxo-6,7-dihydro-5H-[2]pyrindine-6-carboxylic acid ethyl ester (see Robin D. Allan and Joyce Fong, Aust. J. Chem., Vol. 36, Pp. 1221–1226, 1983) and 3,4-(methylenedioxy)aniline. The desired product was obtained as a yellow powder. ESI–MS: m/z 447 (MH$^+$); $^1$H-NMR (CDCl$_3$): δ2.49 (3H, s), 6.26 (2H, s), 7.42 (2H, d, J=8.5 Hz), 7.66 (2H, s), 7.92 (1H, d, J=5 Hz), 8.11 (2H, d, J=8.5 Hz), 8.93 (1H, d, J=5 Hz), 8.99 (1H, brs).

b) Preparation of 6-(2-dimethylamino-ethylamino)-1,3-dioxa-5,9-diaza-indeno[5,6-c]fluoren-7-one This compound was prepared from toluene-4-sulfonic acid 7-oxo-7H-1,3-dioxa-5,9-diaza-indeno[5,6-c]fluoren-6-yl ester obtained above and N,N-dimethylethylenediamine in a similar manner to Example 18d. The desired product was obtained as a reddish powder. ESI–MS: m/z 363 (MH$^+$); $^1$H-NMR (CDCl$_3$): δ2.39 (6H, s), 2.68 (2H, t, J=6 Hz), 3.78 (2H, quartet like, J=ca 6 Hz), 6.12 (2H, s), 7.08 (1H, s), 7.23 (1H, brt J=ca 6 Hz), 7.41 (1H, s), 7.80 (1H, d, J=5 Hz), 8.83 (1H, d, J=5 Hz), 8.86 (1H, s).

EXAMPLE 23

Preparation of 6-(2-dimethylamino-ethylamino)-3-methylsulfanyl-5,9-diaza-benzo[c]fluoren-7-one a) Preparation toluene-4-sulfonic acid 3-methylsulfanyl-7-oxo-7H-5,9-diaza-benzo[c]-fluoren-6-yl ester In a similar manner to Examples 18a–18c, toluene-4-sulfonic acid 3-methylsulfanyl-7-oxo-7H-5,9-diaza-benzo[c]fluoren-6-yl ester was obtained starting from 5,7-dioxo-6,7-dihydro-5H-[2]pyrindine-6-carboxylic acid ethyl ester (see Robin D. Allan and Joyce Fong, Aust. J. Chem., Vol. 36, Pp. 1221–1226, 1983) and 3 (methylthio)aniline. The desired product was obtained as a yellow powder. ESI MS: m/z 449 (MH$^+$); $^1$H-NMR (CDCl$_3$): δ2.50 (3H, s), 2.66 (3H, s), 7.43 (2H, d, J=8 Hz), 7.55 (1H, dd, J=9 Hz, 2 Hz), 7.72 (1H, d, J=2 Hz), 7.98 (1H, dd, J=5 Hz, 1 Hz), 8.14 (2H, d, J=8 Hz), 8.26 (1H, d, J=9 Hz), 8.94 (1H, d, J=5 Hz), 8.99 (1H, d, J=1 Hz).

b) Preparation of 6-(2-dimethylamino-ethylamino)-3-methylsulfanyl-5,9-diaza-benzo[c]fluoren-7-one This compound was prepared from toluene-4-sulfonic acid 3-methylsulfanyl-7-oxo-7H-5,9-diaza-benzo[c]fluoren-6-yl ester obtained above and N,N-dimethylethylenediamine in a similar manner to Example 18d. The desired product was obtained as a reddish powder. ESI–MS: m/z 365 (MH$^+$); $^1$H-NMR (CDCl$_3$): δ2.37 (6H, s), 2.62 (3H, s), 2.66 (2H, t, J=6 Hz), 3.78 (2H, quartet like, J=ca 6 Hz), 7.16 (1H, dd, J=9 Hz, 2 Hz), 7.35 (1H, brt, J=ca 5 Hz), 7.41 (1H, d, J=2 Hz), 7.88 (1H, dd, J=5 Hz, 1 Hz), 8.00 (1H, d, J=9 Hz), 8.85 (1H, d, J=5 Hz), 8.87 (1H, d, J=1 Hz).

EXAMPLE 24

Preparation of 3-methoxy-4-methyl-6-(2-pyrrolidin-1-yl-ethylamino)-5,10-diaza-benzo[c]fluoren-7-one This compound was prepared from toluene-4-sulfonic acid 3-methoxy-4-methyl-7-oxo-7H-5,10-diaza-benzo[c]fluoren-6-yl ester (Example 18c-1) and 1-(2-aminoethyl)pyrrolidine in a similar manner to Example 18d. The desired product was obtained as a reddish powder. ESI–MS: m/z 389 (MH$^+$); $^1$H-NMR (CDCl$_3$): δ1.86 (4H, m), 2.50 (3H, s), 2.72 (4H, m), 2.90 (2H, t, J=6.5 Hz), 3.89 (2H, quartet like, J=ca 6.5 Hz), 4.02 (3H, s), 7.12 (1H, d, J=9 Hz), 7.18 (1H, brt, J=ca 5 Hz), 7.54 (1H, dd, J=4.5 Hz, 1 Hz), 8.04 (1H, d, J=9 Hz), 8.80 (1H, d, J=4.5 Hz), 9.27 (1H, brs).

EXAMPLE 25

Preparation of 6-(2-dimethylamino-ethylamino)-3-methoxy-9-methyl-5,10-diaza-benzo[c]fluoren-7-one a) Preparation of 3-methyl-5,7-dioxo-6,7-dihydro-5H-[2]pyrindine-6-carboxylic acid ethyl ester 6-Methyl-pyridine-3,4-dicarboxylic acid (440 mg) (see Emil J. Moriconi and Francis A. Spano, J. Am. Chem. Soc., Vol. 86, Pp. 38–46, 1964) was suspended in acetic anhydride (10 ml) and the mixture was refluxed for 10 minutes. Ethyl acetoacetate (0.325 ml) and triethylamine (0.745 ml) were dropwise added to the mixture at room temperature and the mixture was stirred overnight. The mixture was concentrated to dryness and purified by silica gel column chromatography developed by dichloromethane and by dichloromethane-methanol (15:1). The desired compound was obtained as a dark red oil which contained 1 equivalent of triethylamine. ESI–MS: m/z 234 (MH$^+$); $^1$H-NMR (CDCl$_3$): δ1.26–1.38 (15H, m), 2.63 (3H, s), 3.28 (6H, q, J=3.3 Hz), 4.22 (2H, q, J=4.2 Hz), 7.29 (1H, s), 8.58 (1H, s).

b) Preparation of 3-methyl-5,7-dioxo-6,7-dihydro-5H-[2]pyrindine-6-carboxylic acid (3-methoxy-phenyl)-amide In a similar manner to Example 1a, 3-methyl-5,7-dioxo-6,7-dihydro-5H-[2]pyrindine-6-carboxylic acid (3-methoxy-phenyl)-amide was obtained starting from the compound of Example 25a. The desired product was obtained as a yellowish red powder. ESI–MS: m/z 311 (MH$^+$); $^1$H-NMR (DMSO-d6): δ2.54 (3H, s), 3.74 (3H, s), 6.51 (1H, ddd, J=8.3 Hz, 2.3 Hz, 1.0 Hz), 6.99 (1H, ddd, J=7.9 Hz, 1.98 Hz, 1.0 Hz), 7.13 (1H, t-like, J=7.9 Hz), 7.18 (1H, d, J=1 Hz), 7.41 (1H, t-like, J=2.3 Hz), 8.35 (1H, d, J=1.0 Hz), 10.80 (1H, s).

c) Preparation of a mixture of 3-methoxy-9-methyl-5H-5,10-diaza-benzo[c]fluorene-6,7-dione and 3-methoxy-10-methyl-5H-5,9-diaza-benzo[c]fluorene-6,7-dione In a similar manner to Example 1b, a mixture of 3-methoxy-9-methyl-5H-5,10-diaza-benzo[c]fluorene-6,7-dione and 3-methoxy-10-methyl-5H-5,9-diaza-benzo[c]fluorene-6,7-dione was obtained as a dark brown solid starting from the compound of Example 25b: ESI–MS: m/z 293 (MH$^+$).

d) Preparation of toluene-4-sulfonic acid 3-methoxy-9-methyl-7-oxo-7H-5,10-diaza-benzo[c]fluoren-6-yl ester In a similar manner to Example 18c, toluene-4-sulfonic acid 3-methoxy-9-methyl-7-oxo-7H-5,10-diaza-benzo[c]fluoren-6-yl ester was obtained starting from the compound of Example 25c. The desired product was obtained as a yellow powder. ESI–MS: m/z 447 (MH$^+$); $^1$H-NMR (CDCl$_3$): δ2.48 (3H, s), 2.71 (3H, s), 4.02 (3H, s), 7.35–7.38 (2H, m), 7.44 (2H, d, J=5.9 Hz), 7.49 (1H, s), 8.13 (2H, d, J=5.9 Hz), 8.29 (1H, d, J=6.8 Hz), 9.24 (1H, s).

e) Preparation of 6-(2-dimethylamino-ethylamino)-3-methoxy-9-methyl-5,10-diaza-benzo[c]fluoren-7-one In a similar manner to Example 18d, 6-(2-dimethylamino-ethylamino)-3-methoxy-9-methyl-5,10-diaza-benzo[c]fluoren-7-one was obtained starting from the compound of Example 25d and N,N-dimethylethylenediamine. The desired product was obtained as a reddish powder. ESI–MS: m/z 363 (MH$^+$); $^1$H-NMR (CDCl$_3$): δ2.35 (6H, s), 2.64 (2H, t, J=6.3 Hz), 2.68 (3H, s), 3.77 (2H, q-like, J=6.3 Hz), 3.97 (3H, s), 6.98 (1H, dd, J=2.6 Hz, 8.9 Hz), 7.06 (1H, d, J=2.6 Hz), 7.31 (1H, brt, J=ca 6 Hz), 7.40 (1H, s), 8.02 (1H, d, J=8.9 Hz), 9.10 (1H, s).

EXAMPLE 26

Preparation of 6-(2-dimethylamino-ethylamino)-3-methoxy-8-methyl-5,9-diaza-benzo[c]fluoren-7-one a) Preparation of 1-methyl-5,7-dioxo-6,7-dihydro-5H-[2]pyrindine-6-carboxylic acid ethyl ester In a similar manner to Example 25a, 1-methyl-5,7-dioxo-6,7-dihydro-5H-[2]pyrindine-6-carboxylic acid ethyl ester was obtained starting from 2-methyl-pyridine-3,4-dicarboxylic acid (see Emil J. Moriconi and Francis A. Spano, J. Am. Chem. Soc., Vol. 86, Pp. 38–46, 1964). The desired product was obtained as a red orange powder. ESI–MS: m/z 234 (MH$^+$); $^1$H-NMR (CDCl$_3$): δ1.35 (3H, t, J=7.3 Hz), 2.81 (3H, s), 4.21 (2H, q, J=7.3 Hz), 7.29 (1H, d, J=4.6 Hz), 8.53 (1H, d, J=4.6 Hz).

b) Preparation of 1-methyl-5,7-dioxo-6,7-dihydro-5H-[2]pyrindine-6-carboxylic acid (3-methoxy-phenyl)-amide In a similar manner to Example 1a, 1-methyl-5,7-dioxo-6,7-dihydro-5H-[2]pyrindine-6-carboxylic acid (3-methoxy-phenyl)-amide was obtained starting from the compound of Example 26a. The desired product was obtained as an orange powder. ESI–MS: m/z 311 (MH$^+$); $^1$H-NMR (DMSO-d6): δ2.88 (3H, s), 3.74 (3H, s), 6.54 (1H, d, J=8.3 Hz), 7.02 (1H, d, J=7.9 Hz), 7.16 (1H, dd, J=7.9 Hz, 8.3 Hz), 7.41 (1H, brs), 7.70 (1H, d, J=5.3 Hz), 8.85 (1H, d, J=5.3 Hz), 10.62 (1H, s).

c) Preparation of a mixture of 3-methoxy-8-methyl-5H-5,9-diaza-benzo[c]fluorene-6,7-dione and 3-methoxy-11-methyl-5H-5,10-diaza-benzo[c]fluorene-6,7-dione In a similar manner to Example 1b, a mixture of 3-methoxy-8-methyl-5H-5,9-diaza-benzo[c]fluorene-6,7-dione and 3-methoxy-11-methyl-5H-5,10-diaza-benzo[c]fluorene-6,7-dione was obtained as a dark brown solid. ESI–MS: m/z 293 (MH$^+$).

d) Preparation of toluene-4-sulfonic acid 3-methoxy-8-methyl-7-oxo-7H-5,9-diaza-benzo[c]fluoren-6-yl ester In a similar manner to Example 18c, toluene-4-sulfonic acid 3-methoxy-8-methyl-7-oxo-7H-5,9-diaza-benzo[c]fluoren-6-yl ester was obtained as an yellow powder starting from the compound of Example 26c. ESI–MS: m/z 447 (MH$^+$); $^1$H-NMR (CDCl$_3$): δ2.49 (3H, s), 2.90 (3H, s), 4.01 (3H, s), 7.00–7.38 (2H, m), 7.43 (2H, d, J=7.9 Hz), 7.85 (1H, d, J=4.9 Hz), 8.15 (2H, d, J=7.9 Hz), 8.33 (1H, d, J=9.9 Hz), 8.79 (1H, d, J=4.9 Hz).

e) Preparation of 6-(2-dimethylamino-ethylamino)-3-methoxy-8-methyl-5,9-diaza-benzo[c]fluoren-7-one In a similar manner to Example 18d, 6-(2-dimethylamino-ethylamino)-3-methoxy-8-methyl-5,9-diaza-benzo[c]fluoren-7-one was obtained starting from the compound of Example 26d and N,N-dimethylethylenediamine. The desired product was obtained as a reddish powder. ESI–MS: m/z 363 (MH$^+$); $^1$H-NMR (CDCl$_3$): δ2.36 (6H, s), 2.64 (2H, t, J=6.3 Hz), 2.87 (3H, s), 3.78 (2H, q-like, J=6.3 Hz), 3.96 (3H, s), 6.97 (1H, dd, J=2.6 Hz, 9.2 Hz), 7.09 (1H, d, J=2.6 Hz), 7.39 (1H, brt, J=ca 6 Hz), 7.75 (1H, d, J=4.9 Hz), 8.07 (1H, d, J=9.2 Hz), 8.71 (1H, d, J=4.9 Hz).

EXAMPLE 27

Preparation of 11-chloro-6-(2-dimethylamino-ethylamino)-3-methoxy-5,10-diaza-benzo[c]fluoren-7-one a) Preparation of 1-chloro-5,7-dioxo-6,7-dihydro-5H-[2]pyrindine-6-carboxylic acid ethyl ester In a similar manner to Example 25a, 1-chloro-5,7-dioxo-6,7-dihydro-5H-[2]-pyrindine-6-carboxylic acid ethyl ester was obtained starting from 2-chloro-pyridine-3,4-dicarboxylic acid (see Florence Mongin, Francois Trecourt and Guy Queguiner, Tetrahedron Lett., Vol. 40, Pp. 5483–5486, 1999). The desired product was obtained as a yellow powder. ESI–MS: m/z 254 (MH$^+$); $^1$H-NMR (DMSO-d6): δ1.18 (3H, t, J=6.9 Hz), 4.02 (2H, q, J=6.9 Hz), 7.33 (1H, d, J=4.3 Hz), 8.49 (1H, d, J=4.3 Hz).

b) Preparation of 1-chloro-5,7-dioxo-6,7-dihydro-5H-[2]pyrindine-6-carboxylic acid (3-methoxy-phenyl)-amide In a similar manner to Example 1a, 1-chloro-5,7-dioxo-6,7-dihydro-5H-[2]pyrindine-6-carboxylic acid (3-methoxy-phenyl)-amide was obtained starting from the compound of Example 27a. The desired product was obtained as a yellowish orange powder. ESI–MS: m/z 331 (MH$^+$); $^1$H-NMR (DMSO-d6): δ3.74 (3H, s), 6.52 (1H, dd, J=1.7 Hz, 7.9 Hz), 7.03 (1H, brd, J=8.9 Hz), 7.15 (1H, t-like, J=7.9 Hz), 7.37 (1H, d, J=4.6 Hz), 7.41 (1H, t-like, J=1.7 Hz), 8.53 (1H, d, J=4.3 Hz), 10.70 (1H, s).

c) Preparation of a mixture of 11-chloro-3-methoxy-5H-5,10-diaza-benzo[c]fluorene-6,7-dione and 8-chloro-3-methoxy-5H-5,9-diaza-benzo[c]fluorene-6,7-dione In a similar manner to Example 1b, a mixture of 11-chloro-3-methoxy-5H-5,10-diaza-benzo[c]fluorene-6,7-dione and 8-chloro-3-methoxy-5H-5,9-diaza-benzo[c]fluorene-6,7-dione was obtained starting from the compound of Example 27b as a dark brown solid. ESI–MS: m/z 313 (MH$^+$).

d) Preparation of toluene-4-sulfonic acid 11-chloro-3-methoxy-7-oxo-7H-5,10-diaza-benzo[c]fluoren-6-yl ester In a similar manner to Example 18c, toluene-4-sulfonic acid 11-chloro-3-methoxy-7-oxo-7H-5,10-diaza-benzo[c]fluoren-6-yl ester was obtained as an yellow powder starting from the compound of Example 27c. ESI–MS: m/z 467 (MH$^+$); $^1$H-NMR (CDCl$_3$): δ2.49 (3H, s), 4.02 (3H, s), 7.32 (1H, dd, J=2.3 Hz, 9.2 Hz), 7.36 (1H, d, J =2.3 Hz), 7.43 (2H, d, J=7.9 Hz), 7.63 (1H, d, J=4.3 Hz), 8.12 (2H, d, J=7.9 Hz), 8.68 (1H, d, J=4.3 Hz), 9.20 (1H, d, J=9.2 Hz).

e) Preparation of 11-chloro-6-(2-dimethylamino-ethylamino)-3-methoxy-5,10-diaza-benzo[c]fluoren-7-one To a solution of N,N-dimethylethylenediamine (1 ml) in dichloromethane (4 ml) was added 11-chloro-3-methoxy-7-oxo-7H-5,10-diaza-benzo[c]fluoren-6-yl ester (Example 27d) (100 mg) and the mixture was stirred overnight under N$_2$. The solution was washed with saturated ammonium chloride aqueous solution and dried over anhydrous sodium sulfate and evaporated to dryness. The residue was purified by silica gel column chromatography developed by dichloromethane-methanol=50:1 and dichloromethane-methanol 9:1. The desired product was obtained as a dark red powder. ESI–MS: m/z 383 (MH$^+$); $^1$H-NMR (CDCl$_3$): δ2.36 (6H, s), 2.65 (2H, t, J=6.3 Hz), 3.78 (2H, q-like, J=6.3 Hz), 3.97 (3H, s), 6.93 (1H, dd, J=2.6 Hz, 9.6 Hz), 7.05 (1H, d, J=2.6 Hz), 7.54 (2H, d, J=4.3 Hz), and 8.60 (2H, d, J=4.3 Hz), 8.98 (1H, d, J=9.6 Hz).

EXAMPLE 28

Preparation of 6-(2-dimethylamino-ethylamino)-3-methoxy-11-methylamino-5,10-diaza-benzo[c]fluoren-7-one To a solution of methylamine (1 ml, 40% in methanol) in dichloromethane (1 ml) was added 11-chloro-6-(2-dimethylamino-ethylamino)-3-methoxy-5,10-diaza-benzo[c]fluoren-7-one (Example 27e) (5.7 mg) and the mixture was stirred at 50° C. for 2 days in a sealed tube. The solution was diluted with dichloromethane and washed with saturated ammonium chloride aqueous solution and dried over anhydrous sodium sulfate and evaporated to dryness. The residue was purified by silica gel thin layer chromatography developed by dichloromethane-methanol=4:1. The desired product was obtained as a dark red powder (1.8 mg). ESI–MS: m/z 378 (MH$^+$); $^1$H-NMR (CDCl$_3$): δ2.44 (6H, s), 2.77 (2H, t, J=6.3 Hz), 3.14 (3H, d, J=4.9 Hz), 3.82 (2H, q-like, J=6.3 Hz), 3.96 (3H, s), 4.85 (1H, brq, J=ca 5 Hz), 6.89–6.95 (2H, m), 7.04 (1H, d, J=2.6 Hz), 7.30 (1H, brt, J=ca 6 Hz), 8.34 (1H, d, J=9.2 Hz), 8.41 (1H, d, J=4.3 Hz).

EXAMPLE 29

Preparation of 6,11-bis-(2-dimethylamino-ethylamino)-3-methoxy-5,10-diaza-benzo[c]fluoren-7-one 23 mg. of 11-chloro-6-(2-dimethylamino-ethylamino)-3-methoxy-5,10-diaza-benzo[c]fluoren-7-one (Example 27e) was suspended in N,N-dimethylethylenediamine (2.0 ml) and the mixture was stirred at 60° C. overnight under nitrogen. The solution was diluted with dichloromethane and washed with saturated ammonium chloride aqueous solution and dried over anhydrous sodium sulfate and evaporated to dryness. The residue was purified by silica gel thin layer chromatography developed by dichloromethane-methanol-25% ammonia solution=100:5:1. The desired product was obtained as a dark red powder (17 mg). ESI–MS: m/z 435 (MH$^+$); $^1$H-NMR (CDCl$_3$): δ2.27 (6H, s), 2.34 (6H, s), 2.60–2.66 (4H, m), 3.60 (2H, q-like, J=6.6 Hz), 3.75 (2H, q-like, J=6.3 Hz), 3.96 (3H, s), 5.76 (1H, brt, J=ca 6 Hz), 6.84 (1H, dd, J=2.6 Hz, 9.6 Hz), 6.92 (1H, d, J=4.6 Hz), 7.04 (1H, d, J=2.6 Hz), 7.36 (1H, brt, J=ca 6 Hz), 8.27 (1H, d, J=4.6 Hz), 8.49 (1H, d, 9.6 Hz).

EXAMPLE 30

Preparation of 11-(3-dimethylamino-2,2-dimethyl-propylamino)-6-(2-dimethylamino-ethylamino)-3-methoxy-5,10-diaza-benzo[c]fluoren-7-one In a similar manner to Example 29, 11-(3-dimethylamino-2,2-dimethyl-propylamino)-6-(2-dimethylamino-ethylamino)-3-methoxy-5,10-diaza-benzo[c]fluoren-7-one was obtained as a dark red powder starting from the compound of Example 27e. ESI–MS: m/z 477 (MH$^+$); $^1$H-NMR (CDCl$_3$): δ1.10 (6H, s), 1.85 (6H, s), 2.24 (2H, s), 2.36 (6H, s), 2.65 (2H, t, J=5.6 Hz), 3.42 (2H, d, J=4.0 Hz), 3.77 (2H, q-like, J=5.6 Hz), 3.95 (3H, s), 6.85–6.89 (2H, m), 7.03 (1H, d, J=2.6 Hz), 7.32 (1H, brt, J=5.6 Hz), 7.99 (1H, brt, J=4.0 Hz), 8.38 (1H, d, J=4.6 Hz), 8.61 (1H, d, J=9.2 Hz).

EXAMPLE 31

Preparation of 11-(3-dimethylamino-2,2-dimethyl-propylamino)-6-(2-dimethylamino-ethylamino)-3-methoxy-4-methyl-5,10-diaza-benzo[c]fluoren-7-one a) Preparation of toluene-4-sulfonic acid 11-chloro-3-methoxy-4-methyl-7-oxo-7H-5,10-diaza-benzo[c]fluoren-6-yl ester In a similar manner to Examples 18a-18c, toluene-4-sulfonic acid 11-chloro-3-methoxy-4-methyl-7-oxo-7H-5,10-diaza-benzo[c]fluoren-6-yl ester was obtained starting from 1-chloro-5,7-dioxo-6,7-dihydro-5H-[2]pyrindine-6-carboxylic acid ethyl ester (Example 27a) and 3-metoxy-2-methyl-phenylamine. The desired product was obtained as an orange powder. ESI–MS: m/z 481 (MH$^+$); $^1$H-NMR (CDCl$_3$): δ2.40 (3H, s), 2.47 (3H, s), 4.06 (3H, s), 7.39 (2H, d, J=8 Hz), 7.41 (1H, d, J=10 Hz), 7.64 (1H, d, J=4.5 Hz), 8.07 (2H, d, J=8 Hz), 8.67 (1H, d, J=4.5 Hz), 9.17 (1H, d, J=10 Hz).

b) Preparation of 11-chloro-6-(2-dimethylamino-ethylamino)-3-methoxy-4-methyl-5,10-diaza-benzo[c]fluoren-7-one This compound was prepared from toluene-4-sulfonic acid 11-chloro-3-methoxy-4-methyl-7-oxo-7H-5,10-diaza-benzo[c]fluoren-6-yl ester obtained above and N,N-dimethylethylenediamine in a similar manner to Example 27e. The desired product was obtained as a brown powder. ESI–MS: m/z 397 (MH$^+$); $^1$H-NMR (CDCl$_3$) δ2.36 (6H, s), 2.51 (3H, s), 2.67 (2H, t, J=6.5 Hz), 3.82 (2H, quartet like, J=ca 6 Hz), 4.02 (3H, s), 7.08 (1H, d, J=9.5 Hz), 7.37 (1H, brt, J=ca 5 Hz), 7.52 (1H, d, J=4.5 Hz,), 8.58 (1H, d, J=4.5 Hz), 8.95 (1H, d, J=9.5 Hz).

c) Preparation of 11-(3-dimethylamino-2,2-dimethyl-propylamino)-6-(2-dimethylamino-ethylamino)-3-methoxy-4-methyl-5,10-diaza-benzo[c]fluoren-7-one This compound was prepared from 11-chloro-6-(2-dimethylamino-ethylamino)-3-methoxy-4-methyl-5,10-diaza-benzo[c]fluoren-7-one obtained above and N,N-2,2-tetramethyl-1,3-propanediamine in a similar manner to Example 29. The desired product was obtained as a reddish powder. ESI–MS: m/z 491 (MH$^+$); $^1$H-NMR (CDCl$_3$): δ1.12 (6H, s), 1.85 (6H, s), 2.24 (2H, s), 2.37 (6H, s), 2.51 (3H, s), 2.68 (2H, t, J=6.5 Hz), 3.42 (2H, d, J=4 Hz), 3.82 (2H, quartet like, J=ca 6 Hz), 3.98 (3H, s,), 6.87 (1H, d, J=4.5 Hz), 6.99 (1H, d, J=9.5 Hz), 7.15 (1H, brt, J=ca 5.5 Hz), 7.86 (1H, brt, J=ca 4 Hz), 8.37 (1H, d, J=4.5 Hz), 8.59 (1H, d, J=9.5 Hz).

EXAMPLE 32

Preparation of 6-(2-dimethylamino-ethylamino)-5,9-diaza-benzo[c]fluoren-7-one a) Preparation of 5,7-dioxo-6,7-dihydro-5H-[2]pyrindine-6-carboxylic acid phenylamide In a similar manner to Example 1a, 5,7-dioxo-6,7-dihydro-5H-[2]pyrindine-6-carboxylic acid phenylamide was obtained starting from 5,7-dioxo-6,7-dihydro-5H-[2]pyrindine-6-carboxylic acid ethyl ester and aniline. The desired product was obtained as a brownish orange powder. ESI–MS: m/z 267 (MH$^+$); $^1$H-NMR (DMSO-d6): δ6.93 (1H, t, J=7.3 Hz), 7.26 (2H, t-like, 7.3 Hz), 7.33 (1H, dd, J=1.4 Hz, 4.6 Hz), 7.59 (2H, d, J=7.3 Hz), 8.51 (1H, d, J=1.4 Hz), 8.72 (1H, d, J=4.6 Hz), 10.78 (1H, brs).

b) Preparation of a mixture of 5H-5,9-diaza-benzo[c]fluorene-6,7-dione and 3-methoxy-11-methyl-5H-5,10-diaza-benzo[c]fluorene-6,7-dione 5,7-Dioxo-6,7-dihydro-5H-[2]pyrindine-6-carboxylic acid phenylamide (1.33 g) obtained above was dissolved in trifluoromethanesulfonic acid (7 ml). The mixture was stirred at 100° C. for 2 days. To the cooled mixture was added ice (40 g). Dark brown ppt was collected with suction and washed with sodium bicarbonate solution and water subsequently to give a mixture (1.2 g) of 5H-5,9-diaza-benzo[c]fluorene-6,7-dione and 3-methoxy-11-methyl-5H-5,10-diaza-benzo[c]fluorene-6,7-dione. ESI–MS: m/z 249 (MH$^+$).

c) Preparation of toluene-4-sulfonic acid 7-oxo-7H-5,9-diaza-benzo[c]fluoren-6-yl ester In a similar manner to Example 18c, toluene-4-sulfonic acid 7-oxo-7H-5,9-diaza-benzo[c]fluoren-6-yl ester was obtained as an yellow powder starting from the compound of Example 32b. ESI–MS: m/z 403 (MH$^+$); $^1$H-NMR (CDCl$_3$): δ2.49 (3H, s), 7.43 (2H, d, 8.4 Hz), 7.76 (1H, ddd, J=1.4 Hz, 7.0 Hz, 8.6 Hz), 7.92 (1H, ddd, J=1.4 Hz, 7.0 Hz, 8.1 Hz), 8.04–8.09 (2H, m), 8.14 (2H, d, J=8.4 Hz), 8.46 (1H, dd, J=8.6 Hz, 1.4 Hz), 8.96 (1H, d, J=4.9 Hz), 9.01 (1H, d, J=0.5 Hz).

d) Preparation of 6-(2-dimethylamino-ethylamino)-5,9-diaza-benzo[c]fluoren-7-one In a similar manner to Example 1d, 6-(2-dimethylamino-ethylamino)-5,9-diaza-benzo[c]fluoren-7-one was obtained starting from the compound of Example 32c and N,N-dimethylethylenediamine. The desired product was obtained as a reddish powder. ESI–MS: m/z 319 (MH$^+$); $^1$H-NMR (CDCl$_3$): δ2.38 (6H, s), 2.68 (2H, t, J=6.3 Hz), 3.81 (2H, q-like J=6.3 Hz), 7.27–7.37 (2H, m), 7.65–7.77 (2H, m), 7.95 (1H, dd, J=1.0 Hz, 5.0 Hz), 8.18 (1H, d, J=7.6 Hz), 8.86–8.88 (2H, m).

EXAMPLE 33

Preparation of 3-chloro-6-(2-dimethylamino-ethylamino)-5,9-diaza-benzo[c]fluoren-7-one a) Preparation of 5,7-dioxo-6,7-dihydro-5H-[2]pyrindine-6-carboxylic acid (3-chlorophenyl)-amide In a similar manner to Example 1a, 5,7-dioxo-6,7-dihydro-5H-[2]pyrindine-6-carboxylic acid (3-chloro-phenyl)-amide was obtained starting from 5,7-dioxo-6,7-dihydro-5H-[2]pyrindine-6-carboxylic acid ethyl ester and 3-chloro-phenylamine. The desired product was obtained as a brownish orange powder. ESI–MS: m/z 301 (MH$^+$); $^1$H-NMR (DMSO-d6): δ6.96–7.00 (1H, m), 7.27–7.29 (2H, m), 7.35 (1H, dd, J=1.3 Hz, 4.6 Hz), 7.98–7.99 (1H, m), 8.53 (1H, d, J=1.0 Hz), 8.74 (1H, d, J=4.6 Hz), 10.92 (1H, brs).

b) Preparation of a mixture of 3-chloro-5H-5,9-diaza-benzo[c]fluorene-6,7-dione and 3-chloro-5H-5,10-diaza-benzo[c]fluorene-6,7-dione In a similar manner to Example 32b, a mixture of 3-chloro-5H-5,9-diaza-benzo[c]fluorene-6,7-dione and 3-chloro-5H-5,10-diaza-benzo[c]fluorene-6,7-dione was obtained starting from the compound of Example 33a as a dark brown solid. ESI–MS: m/z 283 (MH$^+$).

c) Preparation of toluene-4-sulfonic acid 3-chloro-7-oxo-7H-5,9-diaza-benzo[c]fluoren-6-yl ester In a similar manner to Example 18c, toluene-4-sulfonic acid 3-chloro-7-oxo-7H-5,9-diaza-benzo[c]fluoren-6-yl ester was obtained as an yellow powder starting from the compound of Example 33b. ESI–MS: m/z 437 (MH$^+$); $^1$H-NMR (CDCl$_3$): δ2.50 (3H, s), 7.44 (2H, d, 8.1 Hz), 7.68 (1H, dd, J=2.4 Hz, 9.2 Hz), 7.97–8.00 (2H, m), 8.13 (2H, d, J=8.1 Hz), 8.35 (1H, d, J=9.2 Hz), 8.96 (1H, d, J=4.9 Hz), 8.99 (1H, s).

d) Preparation of 3-chloro-6-(2-dimethylamino-ethylamino)-5,9-diaza-benzo[c]fluoren-7-one In a similar manner to Example 1d, 3-chloro-6-(2-dimethylamino-ethylamino)-5,9-diaza-benzo[c]fluoren-7-one was obtained starting from the compound of Example 33c and N,N-dimethylethylenediamine. The desired product was obtained as a reddish powder. ESI–MS: m/z 353 (MH$^+$); $^1$H-NMR (CDCl$_3$): δ2.43 (6H, s), 2.65 (2H, t, J=6.3 Hz), 3.75 (2H, q-like J=6.3 Hz), 7.25 (1H, dd, J=2.0 Hz, 8.9 Hz), 7.35 (1H, brt, J=6.3 Hz), 7.72 (1H, d, J=2.0 Hz), 7.85 (1H, dd, J=1.1 Hz, 4.9 Hz), 8.04 (1H, d, J=8.9 Hz), 8.86–8.87 (2H, m).

EXAMPLE 34

Preparation of 6-(2-dimethylamino-ethylamino)-3-ethoxy-5,9-diaza-benzo[c]fluoren-7-one a) Preparation of 6-chloro-3-hydroxy-5,9-diaza-benzo[c]fluoren-7-one A mixture of 6-chloro-3-methoxy-5,9-diaza-benzo[c]fluoren-7-one (Example 1c-2)(100 mg) and conc. sulfuric acid was stirred at 160° C. for 6 hours. The reaction mixture was poured into ice water (50 ml) and neutralized with ammonia water (28%). Orange ppt was collected with suction and washed water. The ppt was purified by silica gel column chromatography developed by dichloromethane-methanol (50:1) to give 6-chloro-3-hydroxy-5,9-diaza-benzo[c]fluoren-7-one (76 mg) as an orange powder. ESI-MS: m/z 283 (MH$^+$); $^1$H-NMR (DMSO-d6): δ7.26 (1H, d, J=2.5 Hz), 7.38 (1H, dd, J=9 Hz, 2.5 Hz), 8.42 (1H, d, J=5.5 Hz), 8.64 (1H, d, J=9 Hz), 8.88 (1H, s), 8.96 (1H, d, J=5.5 Hz), 11.30 (1H brs).

b) Preparation of 6-chloro-3-ethoxy-5,9-diaza-benzo[c]fluoren-7-one

To a suspension of 6-chloro-3-hydroxy-5,9-diaza-benzo[c]fluoren-7-one (Example 34a) (30 mg) and potassium carbonate (60 mg) in N,N-dimethylformamide (0.5 ml) was added iodoethane (25 mg) and the mixture was stirred at 90° C. for 1.5 hrs. The reaction mixture was diluted with dichloromethane and washed with water and brine. The organic solvent was dried over anhydrous sodium sulfate and evaporated to dryness. The residue was purified by silica gel column chromatography developed by dichloromethane-methanol (100:1) to give 6-chloro-3-ethoxy-5,9-diaza-benzo[c]-fluoren-7-one (18 mg) as a yellow powder. ESI–MS: m/z 311 (MH$^+$); $^1$H-NMR (CDCl$_3$): δ1.54 (3H, t, J=7 Hz), 4.25 (2H, q, J=7 Hz), 7.39 (1H, dd, J=9 Hz, 2.5 Hz), 7.43 (1H, d, J=2.5 Hz), 8.10 (1H, d, J=5.5 Hz), 8.35 (1H, d, J=9 Hz), 8.95 (1H, d, J,=5.5 Hz), 9.04 (1H, s).

c) Preparation of 6-(2-dimethylamino-ethylamino)-3-ethoxy-5,9-diaza-benzo[c]fluoren-7-one 6-Chloro-3-ethoxy-5,9-diaza-benzo[c]fluoren-7-one (Example 34b) (14 mg) was suspended in N,N-dimethylethylenediamine (0.3 ml) and the mixture was stirred at 70° C. for 30 min. The reaction mixture was diluted with dichloromethane and washed with saturated ammonium chloride solution and brine. The organic layer was dried over anhydrous sodium sulfate and evaporated to dryness. The residue was purified by preparative thin layer chromatography developed by dichloromethane-methanol-ammonia water (28%)=15:1:0.1. The desired product was obtained as a reddish powder (16 mg). ESI–MS: m/z 363 (MH$^+$); $^1$H-NMR (CDCl$_3$): δ1.50 (3H, t, J=7 Hz), 2.36 (6H, s), 2.65 (2H, t, J=6.5 Hz), 3.78 (2H, quartet like, J=ca 6 Hz), 4.20 (2H, q, J=7 Hz), 6.97 (1H, dd, J=9 Hz, 2.5 Hz), 7.06 (1H, d, J=2.5 Hz), 7.34 (1H, brt, J=ca 5 Hz), 7.87 (1H, dd, J=5 Hz, 1 Hz), 8.04 (1H, d, J=9 Hz), 8.83 (1H, d, J=5 Hz), 8.86 (1H, d, J=1 Hz).

EXAMPLE 35

Preparation of 6-(2-dimethylamino-ethylamino)-3-isopropoxy-5,9-diaza-benzo[c]fluoren-7-one a) Preparation of 6-chloro-3-isopropoxy-5,9-diaza-benzo[c]fluoren-7-one This compound was prepared from 6-chloro-3-hydroxy-5,9-diaza-benzo[c]fluoren-7-one (Example 34a) and 2-bromopropane in a similar manner to Example 34b. The desired product was obtained as a yellow powder. ESI–MS: m/z 325 (MH$^+$); $^1$H-NMR (CDCl$_3$): δ1.47 (6H, d, J=6 Hz), 4.80 (1H, quintet like, J=ca 6 Hz), 7.36 (1H, dd, J=9 Hz, 2.5 Hz), 7.43 (1H, d, J=2.5 Hz), 8.01 (1H, dd, J=5.5 Hz, J=1 Hz), 8.34 (1H, d, J=9 Hz), 8.95 (1H, d, J=5.5 Hz), 9.03 (1H, d, J=1 Hz).

b) Preparation of 6-(2-dimethylamino-ethylamino)-3-isopropoxy-5,9-diaza-benzo[c]-fluoren-7-one This compound was prepared from 6-chloro-3-isopropoxy-5,9-diaza-benzo[c]fluoren-7-one obtained above and N,N-dimethylethylenediamine in a similar manner to Example 34c. The desired product was obtained as a reddish powder. ESI–MS: m/z 377 (MH$^+$); $^1$H-NMR (CDCl$_3$): δ1.44 (6H, d, J=6 Hz), 2.36 (6H, s), 2.65 (2H, t, J=6.5 Hz), 3.78 (2H, quartet like, J=ca 6 Hz), 4.78 (1H, quintet like, J=ca 6 Hz), 6.94 (1H, dd, J=9 Hz, 2.5 Hz), 7.06 (1H, d, J=2.5 Hz), 7.32 (1H, brt, J=ca 5 Hz), 7.87 (1H, dd, J=5 Hz, 1 Hz), 8.04 (1H, d, J=9 Hz), 8.83 (1H, d, J=5 Hz), 8.86 (1H, d, J=1 Hz).

EXAMPLE 36

Preparation of 3-allyloxy-6-(2-dimethylamino-ethylamino)-5,9-diaza-benzo[c]fluoren-7-one a) Preparation of 3-allyloxy-6-chloro-5,9-diaza-benzo[c]fluoren-7-one This compound was prepared from 6-chloro-3-hydroxy-5,9-diaza-benzo[c]fluoren-7-one (Example 34a) and allyl bromide in a similar manner to Example 34b. The desired product was obtained as a yellow powder. ESI–MS: m/z 323 (MH$^+$); $^1$H-NMR (CDCl$_3$): δ4.75 (2H, dt, J=5 Hz, 1 Hz), 5.41 (1H, dq, J=11 Hz, 1 Hz), 5.52 (1H, dq, J=17 Hz, 1 Hz), 6.12 (1H, ddt, J=17 Hz, 11 Hz, 5 Hz), 7.43 (1H, dd, J=8 Hz, 1.5 Hz), 7.45 (1H, s), 8.01 (1H, dd, J=5 Hz, 1 Hz), 8.36 (1H, dd, J=8 Hz, 1.5 Hz), 8.96 (1H, d, J=5 Hz), 9.04 (1H, d, J=1 Hz).

b) Preparation of 3-allyloxy-6-(2-dimethylamino-ethylamino)-5,9-diaza-benzo[c]fluoren-7-one This compound was prepared from 3-allyloxy-6-chloro-5,9-diaza-benzo[c]fluoren-7-one obtained above and N,N-dimethylethylenediamine in a similar manner to Example 34c. The desired product was obtained as a reddish powder. ESI–MS: m/z 375 (MH$^+$); $^1$H-NMR (CDCl$_3$): δ2.37 (6H, s), 2.66 (2H, t, J=6 Hz), 3.78 (2H, quartet like, J=ca 6 Hz), 4.70 (2H, dt, J=5 Hz, 1 Hz), 5.37 (1H, dq, J=10 Hz, 1 Hz), 5.50 (1H, dq, J=17 Hz, 1 Hz), 6.13 (1H, ddt, J=17 Hz, 10 Hz, 5 Hz), 7.01 (1H, dd, J=9 Hz, 2.5 Hz), 7.09 (1H, d, J=2.5 Hz), 7.34 (1H, brt, J=ca 5 Hz), 7.88 (1H, dd, J=5 Hz, 1 Hz), 8.06 (1H, d, J=9 Hz), 8.84 (1H, d, J=5 Hz), 8.86 (1H, d, J=1 Hz).

EXAMPLE 37

Preparation of 6-(2-dimethylamino-ethylsulfanyl)-3-methoxy-5,9-diaza-benzo[c]fluoren-7-one 6-chloro-3-methoxy-5,9-diaza-benzo[c]fluoren-7-one (Example 1c-2) (20 mg) was dissolved in DMF (2 ml). To the solution were added 2-dimethylaminoethanethiol hydrochloride (21 mg), triethylamine (0.04 ml) and 60% NaH in paraffin liquid (Kanto Chemical Co. Inc.: 15 mg). The mixture was stirred at room temperature for 5 hours. The reaction mixture was dissolved in dichloromethane and the mixture was washed with water. The organic layer was dried over anhydrous sodium sulfate and evaporated to dryness. The residue was purified by silica gel TLC developed by dichloromethane-MeOH-ammonia water (25%)=100:10:1. The desired product (19 mg) was obtained as a yellow solid. ESI–MS: m/z 366 (MH$^+$); $^1$H-NMR (CDCl$_3$): δ2.41 (6H, s), 2.75 (2H, m), 3.51 (2H, m), 3.99 (3H, s), 7.20 (1H, dd, J=9 Hz, 2.5 Hz), 7.25 (1H, d, J=2.5 Hz), 7.86 (1H, dd, J=5 Hz, 1 Hz), 8.13 (1H, d, J=9 Hz), 8.85 (1H, d, 5 Hz), 8.90 (1H, d, J=1 Hz).

EXAMPLE 38

Preparation of 6-(2-dimethylamino-ethoxy)-3-hydroxy-5,9-diaza-benzo[c]fluoren-7-one a) Preparation of 3-benzyloxy-6-chloro-5,9-diaza-benzo[c]fluoren-7-one 6-Chloro-3-hydroxy-5,9-diaza-benzo[c]fluoren-7-one (Example 34a) (27 mg) was dissolved in DMF (2 ml). To the solution were added benzyl chloride (0.016 ml) and potassium carbonate (29 mg). The mixture was stirred at 90° C. for 2 hours. The reaction mixture was dissolved in dichloromethane and the mixture was washed with water. The organic layer was dried over anhydrous sodium sulfate and evaporated to dryness. The residue was purified by silica gel column chromatography developed by dichloromethane and dichloromethane-MeOH=50:1. The desired product (12 mg) was obtained as a light yellow solid. EI–MS: m/z 372 (M$^+$); $^1$H-NMR (CDCl$_3$): δ5.25 (2H, s), 7.30–7.55 (7H, m), 8.00 (1H, dd, J=5 Hz, 1 Hz), 8.36 (1H, d, J=9Hz), 8.95 (1H, d, 5 Hz), 9.03 (1H, d, J=1 Hz).

b) Preparation of 3-benzyloxy-6-(2-dimethylamino-ethoxy)-5,9-diaza-benzo[c]fluoren-7-one The compound of Example 38a (30 mg) was dissolved in DMF (2 ml). To the solution were added 2-dimethylaminoethanol (0.041 ml) and 60% NaH in paraffin liquid (Kanto Chemical Co. Inc.: 4.9 mg). The mixture was stirred at room temperature for 10 minutes. The reaction mixture was dissolved in dichloromethane and the mixture was washed with water. The organic layer was dried over anhydrous sodium sulfate and evaporated to dryness. The residue was purified by silica gel column chromatography developed by dichloromethane and dichloromethane-MeOH=20:1 and dichloromethane and dichloromethane-MeOH=15:1. The desired product (17 mg) was obtained as a yellow solid. ESI–MS: m/z 426 (MH$^+$); $^1$H-NMR (CDCl$_3$): δ2.44 (6H, s), 2.91 (2H, t, J=6 Hz), 4.75 (2H, t, J=6 Hz), 5.24 (2H, s), 7.20–7.55 (7H, m), 7.93 (1H, dd, J=5 Hz, 1 Hz), 8.24 (1H, d, J=9 Hz), 8.88 (1H, d, 5 Hz), 8.93 (1H, d, J=1 Hz).

c) Preparation of 6-(2-dimethylamino-ethoxy)-3-hydroxy-5,9-diaza-benzo[c]fluoren-7-one The compound of Example 38b (12 mg) was dissolved in 95% sulfuric acid (2 ml) and the solution was stirred at room temperature for 30 minutes. The reaction mixture was diluted with water and passed through a Mega Bond Elut SCX (Varian). The column was washed with water and methanol and the product was eluted with ammonia water (25%, Wako Pure Chemical Industries Ltd.)—methanol= 2:98. The eluate was purified by silica gel TLC developed by dichloromethane-MeOH-ammonia water (25%)=50:10:1. The desired product was obtained as a reddish solid. ESI–MS: m/z 336 (MH$^+$); $^1$H-NMR (MeOH-d4): δ2.71 (6H, s), 3.21 (2H, t, J=5.5 Hz), 4.69 (2H, t, J=5.5 Hz), 6.96 (1H, d, J=2.5 Hz), 7.04 (1H, dd, J=9 Hz, 2.5 Hz), 8.02 (1H, d, J=5 Hz), 8.14 (1H, d, J=9 Hz), 8.67 (1H, s), 8.74 (1H, d, J=5 Hz).

EXAMPLE 39

Preparation of 3-hydroxy-6-(2-pyrrolidin-1-yl-ethylamino)-5,10-diaza-benzo[c]fluoren-7-one The compound of Example 3 (11.8 mg) was dissolved in a mixture of acetic acid (0.5 ml) (Wako Pure Chemical Industries Ltd.) and 47% hydrobromic acid (0.5 ml) (Wako Pure Chemical Industries Ltd.) and refluxed for 23 hours. The reaction mixture was diluted with methanol and passed through a Mega Bond Elut SCX (Varian). The column was washed with methanol and the product was eluted with ammonia water (25%, Wako Pure Chemical Industries Ltd.)—methanol=3:97. The eluate was purified by silica gel TLC developed by dichloromethane-MeOH-ammonia water (25%)=100:10:1. The desired product was obtained as a reddish solid. EI–MS: m/z 360 (M$^+$); $^1$H-NMR (MeOH-d4): δ2.08 (4H, m), 3.26 (6H, m), 3.78 (2H, t, 5.5 Hz), 6.57 (1H, d, J=2.5 Hz), 6.78 (1H, dd, J=9 Hz, 2.5 Hz), 7.42 (1H, dd, J=4.5 Hz, 0.5 Hz), 7.81 (1H, d, J=9 Hz), 8.65 (1H, d, 4.5 Hz), 8.99 (1H, brs).

In a similar manner to Example 39, following compounds of Example 40 to Example 50 were prepared.

EXAMPLE 40

Preparation of 6-(2-dimethylamino-ethylamino)-3-hydroxy-5,10-diaza-benzo[c]fluoren-7-one This compound was obtained starting from the compound of Example 1d as a red solid. EI–MS: m/z 334 (M$^+$); $^1$H-NMR (MeOH-d4): δ2.52 (6H, s), 2.84 (2H, t, 6 Hz), 3.78 (2H, t, J=6 Hz), 6.82 (1H, d, J=2.5 Hz), 6.92 (1H, dd, J=9 Hz, 2.5 Hz), 7.59 (1H, brd, J=4.5 Hz), 8.11 (1H, d, J=9 Hz), 8.75 (1H, d, 4.5 Hz), 9.27 (1H, brs).

EXAMPLE 41

Preparation of 6-(2-dimethylamino-ethylamino)-3-hydroxy-5,9-diaza-benzo[c]fluoren-7-one This compound was obtained starting from the compound of Example 2 as a red solid. EI–MS: m/z 334 (M$^+$); $^1$H-NMR (MeOH-d4): δ2.49 (6H, s), 2.82 (2H, t, 6.5 Hz), 3.78 (2H, t, J=6.5 Hz), 6.86 (1H, d, J=2.5 Hz), 6.92 (1H, dd, J=9 Hz, 2.5 Hz), 8.12 (1H, brd, J=5 Hz), 8.15 (1H, d, J=9 Hz), 8.70 (1H, brs), 8.77 (1H, d, J=5 Hz).

EXAMPLE 42

Preparation of 3-hydroxy-6-(2-pyrrolidin-1-yl-ethylamino)-5,9-diaza-benzo[c]fluoren-7-one This compound was obtained starting from the compound of Example 6 as a red solid. ESI–MS: m/z 361 (MH$^+$); $^1$H-NMR (MeOH-d4): δ1.99 (4H, m), ca 3.25 (6H, m), 3.82 (2H, t, J=5.5 Hz), 6.76 (1H, d, J=2.5 Hz), 6.88 (1H, dd, J=9 Hz, 2.5 Hz,), 8.03 (1H, dd, J=5 Hz, 0.5 Hz), 8.08 (1H, d, J=9 Hz), 8.62 (1H, d, 0.5 Hz), 8.69 (1H, d, J=5 Hz).

EXAMPLE 43

Preparation of 3-hydroxy-6-(2-morpholin-4-yl-ethylamino)-5,9-diaza-benzo[c]fluoren-7-one This compound was obtained starting from the compound of Example 7 as a red solid. EI–MS: m/z 376 (M$^+$); $^1$H-NMR (MeOH-d4): δ2.59 (4H, m), 2.71 (2H, t, J=6 Hz), 3.75 (6H, m), 6.95 (1H, dd, J=9 Hz, 2.5 Hz), 6.98 (1H, brs), 8.19 (1H, brd, J=5 Hz), 8.23 (1H, d, J=9 Hz), 8.73 (1H, brs), 8.80 (1H, d, J=5 Hz).

EXAMPLE 44

Preparation of 6-[(2-dimethylamino-ethyl)-methyl-amino]-3-hydroxy-5,9-diaza-benzo[c]fluoren-7-one This compound was obtained starting from the compound of Example 8 as a red solid. EI–MS: m/z 348 (M$^+$); $^1$H-NMR (MeOH-d4): δ2.60 (6H, s), 3.00 (2H, t, J=6.5 Hz), 3.18 (3H, s), 3.77 (2H, t, J=6.5 Hz), 6.71 (1H, d, J=2.5 Hz), 6.89 (1H, dd, J=9 Hz, 2.5 Hz)), 8.01 (1H, brd, J=5 Hz), 8.09 (1H, d, J=9 Hz), 8.63 (1H, brs), 8.69 (1H, d, J=5 Hz).

EXAMPLE 45

Preparation of 6-(2-dimethylamino-ethylamino)-3-hydroxy-4-methyl-5,10-diaza-benzo[c]fluoren-7-one This compound was prepared from the compound of Example 18. The desired product was obtained as a reddish powder. ESI–MS: m/z 349 (MH$^+$); $^1$H-NMR (MeOH-d4:CDCl$_3$=1:1): δ2.44 (6H, s), 2.48 (3H, s), 2.81 (2H, t, J=6.5 Hz), 3.89 (2H, t, J=6.5 Hz), 7.03 (1H, d, J=9 Hz), 7.62 (1H, d, J=4.5 Hz), 7.97 (1H, d, J=9 Hz), 8.76 (1H, d, J=4.5 Hz), 9.24 (1H, brs).

EXAMPLE 46

Preparation of 6-(2-dimethylamino-ethylamino)-3-hydroxy-4-methyl-5,9-diaza-benzo[c]fluoren-7-one This compound was prepared from the compound of Example 19. The desired product was obtained as a reddish powder. ESI–MS: m/z 349 (MH$^+$); $^1$H-NMR (MeOH-d4:CDCl$_3$=1:1): δ2.41 (6H, s), 2.47 (3H, s), 2.77 (2H, t, J=7 Hz), 3.86 (2H, t, J=7 Hz), 6.99 (1H, d, J=9 Hz), 7.94 (1H, d, J=9 Hz), 8.00 (1H, dd, J=5 Hz, 1 Hz), 8.74 (1H, d, J=1 Hz), 8.76 (1H, d, J=5 Hz).

EXAMPLE 47

Preparation of 6-(2-dimethylamino-ethylamino)-3-hydroxy-9-methyl-5,10-diaza-benzo[c]fluoren-7-one 6-(2-Dimethylamino-ethylamino)-3-hydroxy-9-methyl-5,10-diaza-benzo[c]fluoren-7-one was obtained starting from the compound of Example 25e. The desired product was obtained as a reddish powder. ESI–MS: m/z 349 (MH$^+$); $^1$H-NMR (CDCl$_3$-CD$_3$OD 5:2): δ2.44 (6H, s), 2.70 (3H, s), 2.75 (2H, t, J=6.3 Hz), 3.77 (2H, t, J=6.3 Hz), 6.91 (1H, d, J=2.3 Hz), 6.98 (1H, dd, J=9.2 Hz, 2.3 Hz), 7.45 (1H, s), 8.05 (1H, d, J=9.2 Hz), 9.07 (1H, s).

EXAMPLE 48

Preparation of 6-(2-dimethylamino-ethylamino)-3-hydroxy-8-methyl-5,9-diaza-benzo[c]fluoren-7-one 6-(2-Dimethylamino-ethylamino)-3-hydroxy-8-methyl-5,9-diaza-benzo[c]fluoren-7-one was obtained starting from the compound of Example 26e. The desired product was obtained as a reddish powder. ESI–MS: m/z 349 (MH$^+$); $^1$H-NMR (CDCl$_3$-CD$_3$OD 2:1): δ2.42 (6H, s), 2.74 (2H, t, J=6.3 Hz), 2.86 (3H, s), 3.77 (2H, t, J=6.3 Hz), 6.95–6.99 (2H, m), 7.86 (1H, d, J=5.3 Hz), 8.09 (1H, d, J=9.9 Hz), 8.64 (1H, d, J=5.3 Hz).

EXAMPLE 49

Preparation of 3-hydroxy-4-methyl-6-(2-pyrrolidin-1-yl-ethylamino)-5,10-diaza-benzo[c]fluoren-7-one This compound was prepared from the compound of Example 24. The desired product was obtained as a reddish powder. ESI–MS: m/z 375 (MH$^+$); $^1$H-NMR (MeOH-d4:CDCl$_3$=1:1): δ1.88 (4H, m), 2.47 (3H, s), 2.77 (4H, m), 2.95 (2H, t, J=7 Hz), 3.90 (2H, t, J=7 Hz), 7.01 (1H, d, J=9 Hz), 7.61 (1H, d, J=4.5 Hz), 7.93 (1H, d, J=9 Hz), 8.75 (1H, d, J=4.5 Hz), 9.20 (1H, s).

EXAMPLE 50

Preparation of 11-(3-dimethylamino-2,2-dimethyl-propylamino)-6-(2-dimethylamino-ethylamino)-3-hydroxy-4-methyl-5,10-diaza-benzo[c]fluoren-7-one This compound was prepared from the compound of Example 31. The desired product was obtained as a reddish powder. ESI–MS: m/z 477 (MH$^+$); $^1$H-NMR (CDCl$_3$): δ1.07 (6H, s), 1.86 (6H, s), 2.21 (2H, s), 2.41 (6H, s), 2.44 (3H, s), 2.72 (2H, t, J=6 Hz), 3.36 (2H, d, J=4 Hz), 3.76 (2H, quartet like, J=ca 6 Hz), 6.72 (1H, d, J=9 Hz), 6.85 (1H, d, J=4.5 Hz), 7.84 (1H, brs), 8.30 (1H, d, J=9 Hz), 8.34 (1H, d, J=4.5 Hz).

EXAMPLE 51

Preparation of 6-(2-dimethylamino-ethylamino)-3-hydroxy-5,9-diaza-benzo[c]fluoren-7-one oxime The compound of Example 41(18.0 mg) and hydroxylammonium hydrochloride (20.0 mg) (Tokyo Kasei Ltd.) were dissolved in pyridine (0.5 ml) (Wako Pure Chemical Industries Ltd.) and the solution was stirred at 80° C. for 10 hours. The reaction mixture was diluted with dichloromethane and filtered through a glass filter. The solid obtained was dissolved in methanol and passed through a Mega Bond Elut SCX (Varian). The column was washed with methanol and the product was eluted with ammonia water (25%, Wako Pure Chemical Industries Ltd.)—methanol=5:95. The solvent was evaporated to dryness. The desired product was obtained as an orange solid. ESI–MS: m/z 350 (MH$^+$); $^1$H-NMR (MeOH-d4): δ2.45 (6H, s), 2.74 (2H, t, J=6.3 Hz), 3.63 (2H, t, J=6.3 Hz), 6.81 (1H, dd, J=6.6 Hz, 2.3 Hz), 6.93 (1H, d, J=2.3 Hz), 7.77 (1H, d, J=5.3 Hz), 7.83 (1H, d, J=9.2 Hz), 8.42 (1H, d, J=5.3 Hz), 9.16 (1H, s).

Following compounds described in Examples 52 and 53 were prepared from the compound of Example 41 and an appropriate hydroxylamine derivative in a similar manner to Example 51.

EXAMPLE 52

Preparation of 6-(2-dimethylamino-ethylamino)-3-hydroxy-5,9-diaza-benzo[c]fluoren-7-one O-methyl-oxime O-Methylhydroxylamine hydrochloride was used for hydroxylammonium chloride. This compound was obtained as an orange solid. ESI–MS: m/z 364 (MH$^+$); $^1$H-NMR (CDCl$_3$): δ2.35 (6H, s), 2.63 (2H, m), 3.67 (2H, m), 4.34 (3H, s), 6.74 (1H, d, J=8.9 Hz), 7.26–7.49 (3H, m), 8.41 (1H, d, J=5.0 Hz), 9.28 (1H, s).

EXAMPLE 53

Preparation of 6-(2-dimethylamino-ethylamino)-3-hydroxy-5,9-diaza-benzo[c]fluoren-7-one O-allyl-oxime O-Allylhydroxylamine hydrochloride was used for hydroxylammonium chloride. This compound was obtained as an orange solid. ESI–MS: m/z 390 (MH$^+$); $^1$H-NMR (MeOH-d4): δ2.44 (6H, s), 2.74 (2H, t, J=6.3 Hz), 3.72 (2H, t, J=6.3 Hz), 4.96 (2H, d, J=6.6 Hz), 5.37–5.54 (2H, m), 6.17–6.31 (1H, m), 6.90 (1H, d, J=8.9 Hz), 7.00 (1H, d, J=3.0 Hz), 8.05 (1H, d, J=5.3 Hz), 8.08 (1H, brs), 8.61 (1H, d, J=5.3 Hz), 9.23 (1H, s).

EXAMPLE 54

Preparation of 6-(2-dimethylamino-ethylamino)-3-hydroxy-4-methyl-5,9-diaza-benzo[c]fluoren-7-one O-methyl-oxime This compound was prepared from the compound of 6-(2-dimethylamino-ethylamino)-3-hydroxy-4-methyl-5,9-diaza-benzo[c]fluoren-7-one (Example 46) and O-methylhydroxylamine in a similar manner to 52. The desired product was obtained as an orange powder. ESI-MS: m/z 378 (MH$^+$); $^1$H-NMR (CDCl$_3$): δ2.45 (6H, s), 2.56 (3H, s), 2.79 (2H, t, J=6 Hz), 3.86 (2H, quartet like, J=ca 6 Hz), 4.31 (3H, s), 6.78 (1H, d, J=9 Hz), 7.10 (1H, brt, J=ca 6 Hz), 7.72 (1H, d, J=9 Hz), 7.76 (1H, d, J=5 Hz), 8.66 (1H, d, J=5 Hz), 9.41 (1H, s).

EXAMPLE A

Hard gelatin capsules each containing the following ingredients were manufactured in the conventional manner per se:

| | |
|---|---|
| 6-(2-Dimethylamino-ethylamino)-3-methoxy-5,9-diaza-benzo[c]fluoren-7-one | 100 mg |
| Lactose | 56 mg |
| Crystalline Cellulose | 30 mg |
| Silicic acid, Light Anhydrous | 10 mg |
| Talc | 3 mg |
| Magnesium stearate | 1 mg |
| Total | 200 mg |

EXAMPLE B

Tablets each containing the following ingredients were manufactured in the conventional manner per se:

| | |
|---|---|
| 6-(2-Dimethylamino-ethylamino)-3-methoxy-5,9-diaza-benzo[c]fluoren-7-one | 100 mg |
| Lactose | 60 mg |
| Corn starch | 20 mg |
| Sodium Starch Glycolate | 10 mg |
| Polyvinylpyrrolidone | 6 mg |
| Talc | 3 mg |
| Magnesium stearate | 1 mg |
| Total | 200 mg |

EXAMPLE C

Injection solution/emulsion of each containing the following ingredients were manufactured in the conventional manner per se:

| | |
|---|---|
| 6-(2-Dimethylamino-ethylamino)-3-methoxy-5,9-diaza-benzo[c]fluoren-7-one | 50 mg |
| PEG400 | 50–250 mg |
| Lecithin | 100–250 mg |
| Soy oil | 7.5 mg |
| Glycerol | 40–60 mg |
| Water | q.s. 5 ml |

What is claimed is:
1. A polycyclic compound of formula [I],

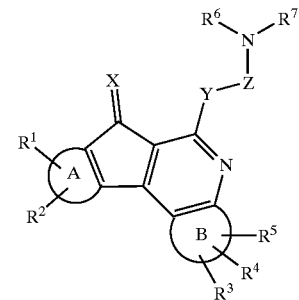

wherein;
ring A is a pyridine, pyrazine, pyridazine or pyrimidine ring which may be substituted by $R^1$ and $R^2$;

$R^1$ and $R^2$ are independently hydrogen, halogen, (C1–C5) alkyl, hydroxy, mercapto, (C1–C5) alkoxy, (C4–C7) cycloalkyloxy, (C3–C7)cycloalkyl(C1–C5)alkyloxy, (C1–C5) alkylthio, (C1–C5) alkylsulfinyl, (C1–C5) alkylsulfonyl, amino, mono-(C1–C5)-alkylamino, di-(C1–C5)-alkylamino or —Y'—Z'—N($R^{6'}$)($R^{7'}$); wherein Y' is O, S or N($R^{9'}$), wherein $R^{9'}$ is hydrogen or (C1–C5) alkyl; or when Y' is N($R^{9'}$), N($R^{9'}$) forms an aliphatic ring together with N($R^{6'}$) and Z';

Z' is (C2–C5) alkylene; or Z' forms an aliphatic ring together with N($R^{6'}$) and (N$R^{9'}$); or Z' forms an aliphatic ring together with N($R^{6'}$);

$R^{6'}$ and $R^{7'}$ are independently hydrogen, (C1–C5) alkyl, (C3–C5) alkenyl, (C3–C7) cycloalkyl, (C4–C7) cycloalkyl, (C3–C7)cycloalkyl(C1–C5)alkyloxy or aryl(C1–C5)alkyl optionally substituted with one to three substituents selected form the group consisting of hydroxy, (C1–C5) alkoxy, amino, mono-(C1–C5)-alkylamino and di-(C1–C5)-alkylamino; or $R^{6'}$ and $R^{7'}$ form an aliphatic ring optionally containing one to three heteroatom(s) selected from the group consisting of oxygen, nitrogen and sulfur together with the adjacent nitrogen; or $R^{6'}$ forms an aliphatic ring together with the adjacent nitrogen and Z'; or $R^{6'}$ forms an aliphatic ring together with the adjacent nitrogen, N($R^{9'}$) and Z';

ring B is a benzene ring, naphthalene ring or benzene ring substituted with (C1–C5) alkylenedioxy group which is optionally substituted by $R^3$, $R^4$ and $R^5$;

$R^3$, $R^4$ and $R^5$ are independently hydrogen, halogen, hydroxy, mercapto, (C1–C5) alkyl, (C1–C5) halogeno-alkyl, (C1–C5) alkoxy, (C1–C5) halogeno-alkoxy, (C3–C5) alkenyloxy, (C4–C7) cycloalkyloxy, (C3–C7) cycloalkyl(C1–C5) alkyloxy, aryl(C1–C5)alkyloxy, (C1–C5) alkylthio, (C1–C5) alkylsulfinyl, (C1–C5) alkylsulfonyl, amino, mono-(C1–C5)-alkylamino or di-(C1–C5)-alkylamino;

X is O or N—O—$R^8$ wherein $R^8$ is a hydrogen, (C1–C5) alkyl, (C3–C5) alkenyl, (C4–C7)cycloalkyl, (C3–C7) cycloalkyl(C1–C5)alkyl, aryl, or aryl(C1–C5)alkyl;

Y is O, S or N(R⁹) wherein R⁹ is hydrogen or (C1–C5) alkyl; or when Y is N(R⁹), N(R⁹) forms an aliphatic ring together with N(R⁶) and Z;

Z is (C2–C5) alkylene optionally substituted with (C1–C5) alkyl radical(s); or Z forms an aliphatic ring together with N(R⁶) and N(R⁹); or Z forms an aliphatic ring together with N(R⁶); and R⁶ and R⁷ are independently hydrogen, (C1–C5) alkyl, (C3–C5) alkenyl, (C4–C7) cycloalkyl, (C3–C7) cycloalkyl(C1–C5)alkyl or aryl(C1–C5)alkyl optionally substituted with hydroxy, alkoxy, amino, mono-(C1–C5)-alkylamino and di-(C1–C5)-alkylamino; or R⁶ and R⁷ form an aliphatic ring optionally containing one to three heteroatom(s) selected from the group consisting of oxygen, nitrogen and sulfur together with the adjacent nitrogen; or R⁶ forms an aliphatic ring together with the adjacent nitrogen and Z; or R⁶ forms an aliphatic ring together with the adjacent nitrogen, N(R⁹) and Z, or a pharmaceutically acceptable salt thereof.

2. The polycyclic compound according to claim 1, wherein ring A is a pyridine ring.

3. The polycyclic compound according to claim 1, wherein ring B is a benzene, naphthalene or benzo[1,3]dioxole ring.

4. The polycyclic compound according to claim 3, wherein ring B is a benzene ring.

5. The polycyclic compound according to claim 1, wherein one of R¹ and R² is hydrogen, (C1–C5) alkyl or —NHCH₂C(CH₃)₂CH₂N(CH₃)₂.

6. The polycyclic compound according to claim 5, wherein one of R¹ and R² is hydrogen, —CH₃ or —NHCH₂C(CH₃)₂CH₂N(CH₃)₂.

7. The polycyclic compound according to claim 5, wherein one of R¹ and R² is hydrogen.

8. The polycyclic compound according to claim 5, wherein one of R¹ and R² is —CH₃.

9. The polycyclic compound according to claim 5, wherein one of R¹ and R² is —NHCH₂C(CH₃)₂CH₂N(CH₃)₂.

10. The polycyclic compound according to claim 5, wherein R¹ is hydrogen and R² is CH₃.

11. The polycyclic compound according to claim 5, wherein, R¹ and R² are hydrogen.

12. The polycyclic compound according to claim 1, wherein X is O, NOH or NOCH₃.

13. The polycyclic compound according to claim 12, wherein X is O.

14. The polycyclic compound according to claim 12, wherein X is NOCH₃.

15. The polycyclic compound according to claim 12, wherein X is NOH.

16. The polycyclic compound according to claim 1, wherein —Y—Z—N(R⁶)(R⁷) is —NH—CH₂CH₂—N(CH₃)₂ or —NH—CH₂CH₂-(pyrrolidin-1-yl).

17. The polycyclic compound according to claim 16, wherein —Y—Z—N(R⁶)(R⁷) is —NH—CH₂CH₂—N(CH₃)₂.

18. The polycyclic compound according to claim 16, wherein —Y—Z—N(R⁶)(R⁷) is —NH—CH₂CH₂-(pyrrolidin-1-yl).

19. The polycyclic compound according to claim 1, wherein R³, R⁴ and R⁵ are
 a) all hydrogen,
 b) one is fluoro and the two others are hydrogen,
 c) one is hydroxy and the two others are hydrogen,
 d) one is OCH₃ and the two others are hydrogen, or
 e) one is hydrogen, one is hydroxy and the third is CH₃.

20. The polycyclic compounds according to claim 1, wherein R³, R⁴ and R⁵ are
 a) all hydrogen,
 b) R³, R⁴ are hydrogen and R⁵ is hydroxy,
 c) R³, R⁴ are hydrogen and R⁵ is OCH₃, or
 d) R³, is hydrogen, R⁴ is CH₃ and R⁵ is hydroxy.

21. The polycyclic compound according to claim 1, wherein the compound is
 a) 6-(2-dimethylamino-ethylamino)-3-methoxy-5,9-diaza-benzo[c]fluoren-7-one,
 b) 6-(2-dimethylamino-ethylamino)-3-hydroxy-5,9-diaza-benzo[c]fluoren-7-one,
 c) 6-(2-dimethylamino-ethylamino)-5,9-diaza-benzo[c]fluoren-7-one,
 d) 6-(2-dimethylamino-ethylamino)-2-fluoro-3-methoxy-5,9-diaza-benzo[c]-fluoren-7-one,
 e) 6-(2-dimethylamino-ethylamino)-3-hydroxy-4-methyl-5,9-diaza-benzo[c]fluoren-7-one,
 f) 6-(2-dimethylamino-ethylamino)-3-ethoxy-5,9-diaza-benzo[c]fluoren-7-one,
 g) 3-allyloxy-6-(2-dimethylamino-ethylamino)-5,9-diaza-benzo[c]fluoren-7-one,
 h) 3-chloro-6-(2-dimethylamino-ethylamino)-5,9-diaza-benzo[c]fluoren-7-one,
 i) 6-(2-dimethylamino-ethylamino)-1,3-dimethoxy-5,9-diaza-benzo[c]fluoren-7-one, or
 j) 6-(2-dimethylamino-ethylamino)-5,9-diaza-indeno[1,2-a]phenanthren-7-one.

22. The polycyclic compound according to claim 1, wherein the compound is
 a) 6-(2-dimethylamino-ethylamino)-1,3-dioxa-5,9-diaza-indeno[5,6-c]fluoren-7-one,
 b) 6-(2-dimethylamino-ethylamino)-3-methoxy-5,10-diaza-benzo[c]fluoren-7-one,
 c) 6-(2-dimethylamino-ethylamino)-3-hydroxy-5,10-diaza-benzo[c]fluoren-7-one,
 d) 3-hydroxy-6-(2-pyrrolidin-1-yl-ethylamino)-5,10-diaza-benzo[c]fluoren-7-one,
 e) 6-(2-dimethylamino-ethylamino)-3-hydroxy-4-methyl-5,10-diaza-benzo[c]fluoren-7-one,
 f) 3-methoxy-4-methyl-6-(2-pyrrolidin-1-yl-ethylamino)-5,10-diaza-benzo[c]-fluoren-7-one,
 g) 3-hydroxy-4-methyl-6-(2-pyrrolidin-1-yl-ethylamino)-5,10-diaza-benzo[c]fluoren-7-one,
 h) 3-methoxy-6-(2-pyrrolidin-1-yl-ethylamino)-5,9-diaza-benzo[c]fluoren-7-one,
 i) 3-methoxy-6-(2-methylamino-ethylamino)-5,9-diaza-benzo[c]fluoren-7-one, or
 j) 3-methoxy-6-(4-methyl-piperazin-1-yl)-5,9-diaza-benzo[c]fluoren-7-one.

23. The polycyclic compound according to claim 1, wherein the compound is
 a) 3-hydroxy-6-(2-pyrrolidin-1-yl-ethylamino)-5,9-diaza-benzo[c]fluoren-7-one,
 b) 3-hydroxy-6-(2-morpholin-4-yl-ethylamino)-5,9-diaza-benzo[c]fluoren-7-one,
 c) 6-[(2-dimethylamino-ethyl)-methyl-amino]-3-hydroxy-5,9-diaza-benzo[c]fluoren-7-one,
 d) 6-(2-dimethylamino-ethoxy)-3-hydroxy-5,9-diaza-benzo[c]fluoren-7-one, e) 6-(2-dimethylamino-ethylamino)-3-methoxy-9-methyl-5,10-diaza-benzo[c]fluoren-7-one, f) 6,11-bis-(2-dimethylamino-ethylamino)-3-methoxy-5,10-diaza-benzo[c]fluoren-7-one, g) 11-(3-dimethylamino-2,2-dimethyl-propylamino)-6-(2-dimethylamino-ethylamino)-3-methoxy-5,10-diaza-benzo[c]fluoren-7-one, h) 11-(3-dimethylamino-2,2-dimethyl-propylamino)-6-(2-dimethylamino-ethylamino)-3-methoxy-4-methyl-5,10-diaza-benzo[c]fluoren-7-one, i) 6-(2-dimethylamino-ethylamino)-3-hydroxy-9-methyl-5,10-diaza-benzo[c]fluoren-7-one, or j) 6-(2-dimethylamino-ethylamino)-3-hydroxy-8-methyl-5,9-diaza-benzo[c]fluoren-7-one.

24. The polycyclic compound according to claim 1, wherein the compound is a) 11-(3-dimethylamino-2,2-dimethyl-propylamino)-6-(2-dimethylamino-ethylamino)-3-hydroxy-4-methyl-5,10-diaza-benzo[c]fluoren-7-one, b) 6-(2-dimethylamino-ethylamino)-3-hydroxy-5,9-diaza-benzo[c]fluoren-7-one oxime, c) 6-(2-dimethylamino-ethylamino)-3-hydroxy-5,9-diaza-benzo[c]fluoren-7-one O-methyl-oxime, or d) 6-(2-dimethylamino-ethylamino)-3-hydroxy-4-methyl-5,9-diaza-benzo[c]fluoren-7-one O-methyl-oxime.

25. The polycyclic compound according to claim 1, wherein the compound is a) 6-(2-dimethylamino-ethylamino)-3-methoxy-5,9-diaza-benzo[c]fluoren-7-one, b) 6-(2-dimethylamino-ethylamino)-3-hydroxy-5,9-diaza-benzo[c]fluoren-7-one, c) 6-(2-dimethylamino-ethylamino)-5,9-diaza-benzo[c]fluoren-7-one, d) 6-(2-dimethylamino-ethylamino)-3-hydroxy-5,10-diaza-benzo[c]fluoren-7-one, e) 3-hydroxy-6-(2-pyrrolidin-1-yl-ethylamino)-5,10-diaza-benzo[c]fluoren-7-one, f) 6-(2-dimethylamino-ethylamino)-3-hydroxy-4-methyl-5,10-diaza-benzo[c]fluoren-7-one, g) 3-hydroxy-4-methyl-6-(2-pyrrolidin-1-yl-ethylamino)-5,10-diaza-benzo[c]fluoren-7-one, h) 3-hydroxy-6-(2-pyrrolidin-1-yl-ethylamino)-5,9-diaza-benzo[c]fluoren-7-one, i) 6-(2-dimethylamino-ethylamino)-3-hydroxy-9-methyl-5,10-diaza-benzo[c]fluoren-7-one, or j) 11-(3-dimethylamino-2,2-dimethyl-propylamino)-6-(2-dimethylamino-ethylamino)-3-hydroxy-4-methyl-5,10-diaza-benzo[c]fluoren-7-one.

26. A pharmaceutical composition comprising a polycyclic compound according to claim 1 as an active ingredient and a pharmaceutically acceptable carrier.

27. The pharmaceutical composition according to claim 26, wherein the composition is suitable for oral or parenteral administration.

28. A method for treating a cell proliferative disorder comprising administering to a patient in need thereof a therapeutically effective amount of a polycyclic compound of formula [I],

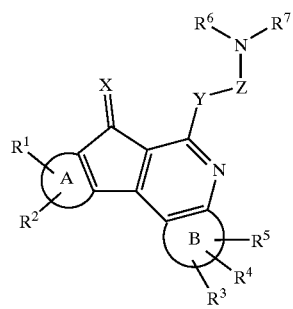

wherein;

ring A is a pyridine, pyrazine, pyridazine or pyrimidine ring which may be substituted by $R^1$ and $R^2$;

$R^1$ and $R^2$ are independently hydrogen, halogen, (C1–C5) alkyl, hydroxy, mercapto, (C1–C5) alkoxy, (C4–C7) cycloalkyloxy, (C3–C7)cycloalkyl(C1–C5)alkyloxy, (C1–C5) alkylthio, (C1–C5) alkylsulfinyl, (C1–C5) alkylsulfonyl, amino, mono-(C1–C5)-alkylamino, di-(C1–C5)-alkylamino or —Y'—Z'—N($R^{6'}$)($R^{7'}$); wherein Y' is O, S or N($R^{9'}$), wherein $R^{9'}$ is hydrogen or (C1–C5) alkyl; or when Y' is N($R^{9'}$), N($R^{9'}$) forms an aliphatic ring together with N($R^{6'}$) and Z';

Z' is (C2–C5) alkylene; or Z' forms an aliphatic ring together with N($R^{6'}$) and (N$R^{9'}$); or Z' forms an aliphatic ring together with N($R^{6'}$);

$R^{6'}$ and $R^{7'}$ are independently hydrogen, (C1–C5) alkyl, (C3–C5) alkenyl, (C3–C7) cycloalkyl, (C4–C7) cycloalkyl, (C3–C7)cycloalkyl(C1–C5)alkyloxy or aryl(C1–C5)alkyl optionally substituted with one to three substituents selected form the group consisting of hydroxy, (C1–C5) alkoxy, amino, mono-(C1–C5)-alkylamino and di-(C1–C5)-alkylamino; or $R^{6'}$ and $R^{7'}$ form an aliphatic ring optionally containing one to three heteroatom(s) selected from oxygen, nitrogen and sulfur together with the adjacent nitrogen; or $R^{6'}$ forms an aliphatic ring together with the adjacent nitrogen and Z' or forms an aliphatic ring together with the adjacent nitrogen, N($R^{9'}$) and Z';

ring B is a benzene ring, naphthalene ring or benzene ring substituted with (C1–C5) alkylenedioxy group which is optionally substituted by $R^3$, $R^4$ and $R^5$;

$R^3$, $R^4$ and $R^5$ are independently hydrogen, halogen, hydroxy, mercapto, (C1–C5) alkyl, (C1–C5) halogeno-alkyl, (C1–C5) alkoxy, (C1–C5) halogeno-alkoxy, (C3–C5) alkenyloxy, (C4–C7) cycloalkyloxy, (C3–C7) cycloalkyl(C1–C5) alkyloxy, aryl(C1–C5)alkyloxy, (C1–C5) alkylthio, (C1–C5) alkylsulfinyl, (C1–C5) alkylsulfonyl, amino, mono-(C1–C5)-alkylamino or di-(C1–C5)-alkylamino;

X is O or N—O—$R^8$ wherein $R^8$ is a hydrogen, (C1–C5) alkyl, (C3–C5) alkenyl, (C4–C7)cycloalkyl, (C3–C7) cycloalkyl(C1–C5)alkyl, aryl, or aryl(C1–C5)alkyl;

Y is O, S or N($R^9$) wherein $R^9$ is hydrogen or (C1–C5) alkyl; or when Y is N($R^9$), N($R^9$) forms an aliphatic ring together with N($R^6$) and Z;

Z is (C2–C5) alkylene optionally substituted with (C1–C5) alkyl radical(s); or Z forms an aliphatic ring together with N($R^6$) and N($R^9$); or Z forms an aliphatic ring together with N($R^6$); and $R^6$ and $R^7$ are independently hydrogen, (C1–C5) alkyl, (C3–C5) alkenyl, (C4–C7) cycloalkyl, (C3–C7)

cycloalkyl(C1–C5)alkyl or aryl(C1–C5)alkyl optionally substituted with hydroxy, alkoxy, amino, mono-(C1–C5)-alkylamino or di-(C1–C5)-alkylamino; or $R^6$ and $R^7$ form an aliphatic ring optionally containing one to three heteroatom(s) selected from the group consisting of oxygen, nitrogen and sulfur together with the adjacent nitrogen;

or $R^6$ forms an aliphatic ring together with the adjacent nitrogen and Z; or $R^6$ forms an aliphatic ring together with the adjacent nitrogen, $N(R^9)$ and Z.

29. The method according to claim 28, wherein the cell proliferative disorder is cancer.

30. The method according to claim 28 wherein the cancer is solid tumor.

31. The method according to claim 28, wherein the cell proliferative disorder is colorectal cancer, lung cancer, breast cancer, stomach cancer, cervical cancer and bladder cancer.

32. A process for producing polycyclic compounds of formula [I],

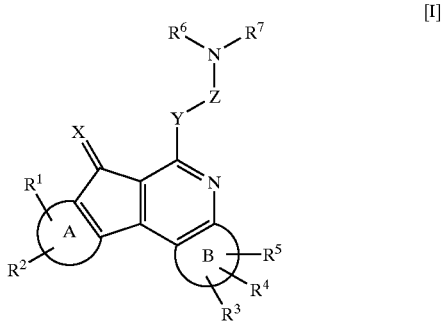

herein ring A is a pyridine, pyrazine, pyridazine or pyrimidine ring which may be substituted by $R^1$ and $R^2$;

$R^1$ and $R^2$ are independently hydrogen, halogen, (C1–C5) alkyl, hydroxy, mercapto, (C1–C5) alkoxy, (C4–C7) cycloalkyloxy, (C3–C7)cycloalkyl(C1–C5)alkyloxy, (C1–C5) alkylthio, (C1–C5) alkylsulfinyl, (C1–C5) alkylsulfonyl, amino, mono-(C1–C5)-alkylamino, di-(C1–C5)-alkylamino or —Y'—Z'—$N(R^{6'})(R^{7'})$; wherein Y' is O, S or $N(R^{9'})$, wherein $R^{9'}$ is hydrogen or (C1–C5) alkyl; or when Y' is $N(R^{9'})$, $N(R^{9'})$ forms an aliphatic ring together with $N(R^{6'})$ and Z';

Z' is (C2–C5) alkylene; or Z' forms an aliphatic ring together with $N(R^{6'})$ and $(NR^{9'})$; or Z' forms an aliphatic ring together with $N(R^{6'})$;

$R^{6'}$ and $R^{7'}$ are independently hydrogen, (C1–C5) alkyl, (C3–C5) alkenyl, (C3–C7) cycloalkyl, (C4–C7) cycloalkyl, (C3–C7)cycloalkyl(C1–C5)alkyl or aryl (C1–C5)alkyl optionally substituted with one to three substituents selected form the group consisting of hydroxy, (C1–C5) alkoxy, amino, mono-(C1–C5)-alkylamino and di-(C1–C5)-alkylamino; or $R^{6'}$ and $R^{7'}$ form an aliphatic ring optionally containing one to three heteroatom(s) selected from oxygen, nitrogen and sulfur together with the adjacent nitrogen; or $R^{6'}$ forms an aliphatic ring together with the adjacent nitrogen and Z'; or $R^{6'}$ forms an aliphatic ring together with the adjacent nitrogen, $N(R^{9'})$ and Z';

ring B is a benzene ring, naphthalene ring or benzene ring substituted with (C1–C5) alkylenedioxy group which is optionally substituted by $R^3$, $R^4$ and $R^5$;

$R^3$, $R^4$ and $R^5$ are independently hydrogen, halogen, hydroxy, mercapto, (C1–C5) alkyl, (C1–C5) halogeno-alkyl, (C1–C5) alkoxy, (C1–C5) halogeno-alkoxy, (C3–C5) alkenyloxy, (C4–C7) cycloalkyloxy, (C3–C7) cycloalkyl(C1–C5) alkyloxy, aryl(C1–C5)alkyloxy, (C1–C5) alkylthio, (C1–C5) alkylsulfinyl, (C1–C5) alkylsulfonyl, amino, mono-(C1–C5)-alkylamino or di-(C1–C5)-alkylamino;

X is O;

Y is O, S or $N(R^9)$ wherein $R^9$ is hydrogen or (C1–C5) alkyl; or when Y is $N(R^9)$, $N(R^9)$ forms an aliphatic ring together with $N(R^6)$ and Z;

Z is (C2–C5) alkylene optionally substituted with (C1–C5) alkyl radical(s); or Z forms an aliphatic ring together with $N(R^6)$ and $N(R^9)$; or Z forms an aliphatic ring together with $N(R^6)$; and $R^6$ and $R^7$ are independently hydrogen, (C1–C5) alkyl, (C3–C5) alkenyl, (C4–C7) cycloalkyl, (C3–C7) cycloalkyl(C1–C5)alkyl or aryl(C1–C5)alkyl optionally substituted with hydroxy, alkoxy, amino, mono-(C1–C5)-alkylamino or di-(C1–C5)-alkylamino; or $R^6$ and $R^7$ form an aliphatic ring optionally containing one to three heteroatom(s) selected from the group consisting of oxygen, nitrogen and sulfur together with the adjacent nitrogen; or $R^6$ forms an aliphatic ring together with the adjacent nitrogen and Z; or $R^6$ forms an aliphatic ring together with the adjacent nitrogen, $N(R^9)$ and Z, which comprises reacting a compound of the formula [VI]

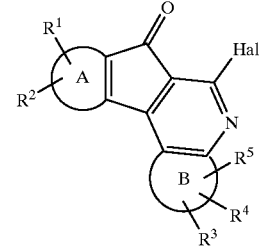

wherein ring A, ring B, $R^1$, $R^2$, $R^3$, $R^4$ and $R^5$ are the same as defined above; Hal is halogen;

with a compound of the formula [VIII],

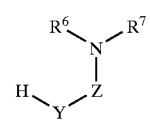

wherein $R^6$, $R^7$, Y and Z are the same as defined above.

33. The process according to claim 32, which comprises substituting —Hal of the compound of formula [VI] by —Y—Z—$N(R^6)(R^7)$ of the compound of formula [VIII].

34. A process for producing polycyclic compounds of formula [I],

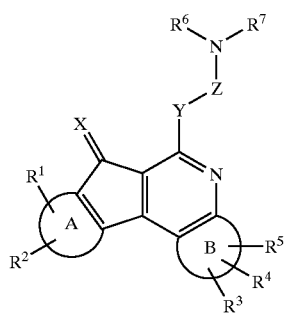

[I]

wherein ring A is a pyridine, pyrazine, pyridazine or pyrimidine ring which may be substituted by $R^1$ and $R^2$;

$R^1$ and $R^2$ are independently hydrogen, halogen, (C1–C5) alkyl, hydroxy, mercapto, (C1–C5) alkoxy, (C4–C7) cycloalkyloxy, (C3–C7)cycloalkyl(C1–C5)alkyloxy, (C1–C5) alkylthio, (C1–C5) alkylsulfinyl, (C1–C5) alkylsulfonyl, amino, mono-(C1–C5)-alkylamino, di-(C1–C5)-alkylamino or —Y'—Z'—N($R^{6'}$)($R^{7'}$); wherein Y' is O, S or N($R^{9'}$), wherein $R^{9'}$ is hydrogen or (C1–C5) alkyl; or when Y' is N($R^{9'}$), N($R^{9'}$) forms an aliphatic ring together with N($R^{6'}$) and Z';

Z' is (C2–C5) alkylene; or Z' forms an aliphatic ring together with N($R^{6'}$) and (N$R^{9'}$); or Z' forms an aliphatic ring together with N($R^{6'}$);

$R^{6'}$ and $R^{7'}$ are independently hydrogen, (C1–C5) alkyl, (C3–C5) alkenyl, (C4–C7) cycloalkyl, (C3–C7) cycloalkyl(C1–C5)alkyl or aryl(C1–C5)alkyl optionally substituted with one to three substituents selected from the group consisting of hydroxy, (C1–C5) alkoxy, amino, mono-(C1–C5)-alkylamino and di-(C1–C5)-alkylamino; or $R^{6'}$ and $R^{7'}$ form an aliphatic ring optionally containing one to three heteroatom(s) selected from the group consisting of oxygen, nitrogen and sulfur together with the adjacent nitrogen; or $R^{6'}$ forms an aliphatic ring together with the adjacent nitrogen and Z'; or $R^{6'}$ forms an aliphatic ring together with the adjacent nitrogen, N($R^{9'}$) and Z';

ring B is a benzene ring, naphthalene ring or benzene ring substituted with (C1–C5) alkylenedioxy group which is optionally substituted by $R^3$, $R^4$ and $R^5$;

$R^3$, $R^4$ and $R^5$ are independently hydrogen, halogen, hydroxy, mercapto, (C1–C5) alkyl, (C1–C5) halogenoalkyl, (C1–C5) alkoxy, (C1–C5) halogeno-alkoxy, (C3–C5) alkenyloxy, (C4–C7) cycloalkyloxy, (C3–C7) cycloalkyl(C1–C5)alkyloxy, aryl(C1–C5)alkyloxy, (C1–C5) alkylthio, (C1–C5) alkylsulfinyl, (C1–C5) alkylsulfonyl, amino, mono-(C1–C5)-alkylamino or di-(C1–C5)-alkylamino;

X is O;

Y is O, S or N($R^9$) wherein $R^9$ is hydrogen or (C1–C5) alkyl; or when Y is N($R^9$), N($R^9$) forms an aliphatic ring together with N($R^6$) and Z;

Z is (C2–C5) alkylene optionally substituted with (C1–C5) alkyl radical(s); or Z forms an aliphatic ring together with N($R^6$) and N($R^9$); or Z forms an aliphatic ring together with N($R^6$); and $R^6$ and $R^7$ are independently hydrogen, (C1–C5) alkyl, (C3–C5) alkenyl, (C4–C7) cycloalkyl, (C3–C7) cycloalkyl, (C1–C5) alkyl or aryl, (C1–C5)alkyl optionally substituted with hydroxy, alkoxy, amino, mono-(C1–C5)-alkylamino or di-(C1–C5)-alkylamino; or $R^6$ and $R^7$ form an aliphatic ring optionally containing one to three heteroatom(s) selected from the group consisting of oxygen, nitrogen and sulfur together with the adjacent nitrogen; or $R^6$ forms an aliphatic ring together with the adjacent nitrogen and Z; or $R^6$ forms an aliphatic ring together with the adjacent nitrogen, N($R^9$) and Z, which comprises reacting a compound of formula [VII],

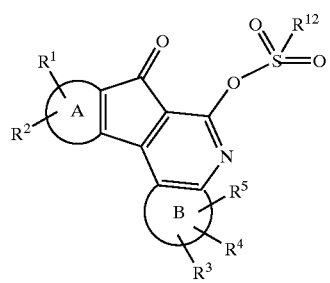

[VII]

wherein ring A, ring B, $R^1$, $R^2$, $R^3$, $R^4$ and $R^5$ are the same as defined above; and $R^{12}$ is (C1–C5) alkyl, (C1–C5) halogenoalkyl or aryl, with a compound of formula [VIII],

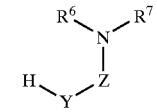

[VIII]

wherein $R^6$, $R^7$, Y and Z are the same as defined above.

35. The process according to claim 34, which comprises substituting —OS(O₂)$R^{12}$ in the compound of formula VII by —Y—Z—N($R^6$)($R^7$) of the compound of formula [VIII].

* * * * *